(12) United States Patent
Jefferies et al.

(10) Patent No.: US 6,361,770 B1
(45) Date of Patent: *Mar. 26, 2002

(54) METHOD OF ENHANCING EXPRESSION OF MHC CLASS I MOLECULES BEARING ENDOGENOUS PEPTIDES

(75) Inventors: Wilfred A. Jefferies, South Surrey; Reinhard Gabathuler, South Vancouver; Gregor S. D. Reid; Gerassimos Kolaitis, both of Vancouver, all of (CA)

(73) Assignee: University of British Columbia, Vancouver (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/817,731

(22) PCT Filed: Sep. 22, 1995

(86) PCT No.: PCT/CA95/00544

§ 371 Date: Jul. 21, 1997

§ 102(e) Date: Jul. 21, 1997

(87) PCT Pub. No.: WO96/09380

PCT Pub. Date: Mar. 28, 1996

Related U.S. Application Data

(63) Continuation of application No. 08/311,442, filed on Sep. 23, 1994, now abandoned.

(51) Int. Cl.⁷ .................. A61K 48/00; A61K 38/00; C12N 15/63
(52) U.S. Cl. ............... 424/93.21; 424/93.1; 435/325; 435/320.1; 514/44
(58) Field of Search .................. 424/93.21, 93.1; 435/325, 320.1; 514/44

(56) References Cited

PUBLICATIONS

Verma et al. (1997) Nature, vol. 389, 239–242, 1997.*
Miller et al. (1995) FASEB, vol. 9, 190–199, 1995.*
Spies et al. (1991) Nature, vol. 351, 323–324, May 1991.*
Momburg et al. (1992) Nature, vol. 360, 174–177, Nov. 1992.*
Franksson et al. (1993) J. Exp. Med., vol. 177, 201–205, Jan. 1993.*
Powis et al. (1991) Nature, vol. 354, 528–531, Dec. 1991.*
Bachmann et al. (1994) Current Opin. Immunol., vol. 6, 320–327, 1994.*
Restifo et al. (1993) J. Immunother., vol. 14, 265–272, Feb. 1993.*
Orkin et al. (1995) "Report and Recommendations of the Panel to Assess the NIH Investment in Research on Gene Therapy", Dec. 1995.*
Monaco, J.J., Immunology Today, vol. 13, No. 5, May 1992, pp. 173–179.
Ossevoort, M.A. et al., European Journal of Immunology, vol. 23, No. 12, 1993, pp. 3082–3088.
Zweerink, H.J., et al., Journal of Immunology, vol. 150, No. 5, Mar. 1, 1993, pp. 1763–1771.
Arnold, D. et al., Nature, vol. 360, No. 6400, Nov. 12, 1992, pp. 171–174.
Momburg, F. et al., Nature, vol. 360, No. 6400, Nov. 12, 1992, pp. 174–177.
Kelly, A. et al., Nature, vol. 355, No. 6361, Feb. 13, 1992, pp. 641–644.
Spies, T. et al., Nature, vol. 355, No. 6361, Feb. 13, 1992, pp. 644–646.
Fruh, K. et al., Journal of Biological Chemistry, vol. 267, No. 31, Nov. 5, 1992, pp. 22131–22140.
Yang, Y. et al., Journal of Biological Chemistry, vol. 267, No. 17, Jun. 15, 1992, 11669–11672.
Jefferies, W.A. et al., The Journal of Immunology, vol. 151, No. 6, Sep. 15, 1993, pp. 2974–2985.

* cited by examiner

*Primary Examiner*—Robert A. Schwartzman
*Assistant Examiner*—Anne Marie S. Beckerleg
(74) *Attorney, Agent, or Firm*—Bereskin & Parr; Micheline Gravelle

(57) ABSTRACT

A method of enhancing expression of MHC Class I molecules bearing endogenous peptides on the surface of a target cell expressing low or nondetectable levels of MHC Class I molecules and expressing low or nondetectable levels of TAP-1 and TAP-2 transporter proteins comprising: introducing into the target cell a nucleic acid molecule comprising a sequence encoding TAP-1 or TAP-2 under control of a suitable promoter; and expressing TAP-1 or TAP-2 in the target cell under suitable conditions, thereby enhancing processing and presentation of MHC Class I molecules bearing endogenous peptides.

10 Claims, 20 Drawing Sheets

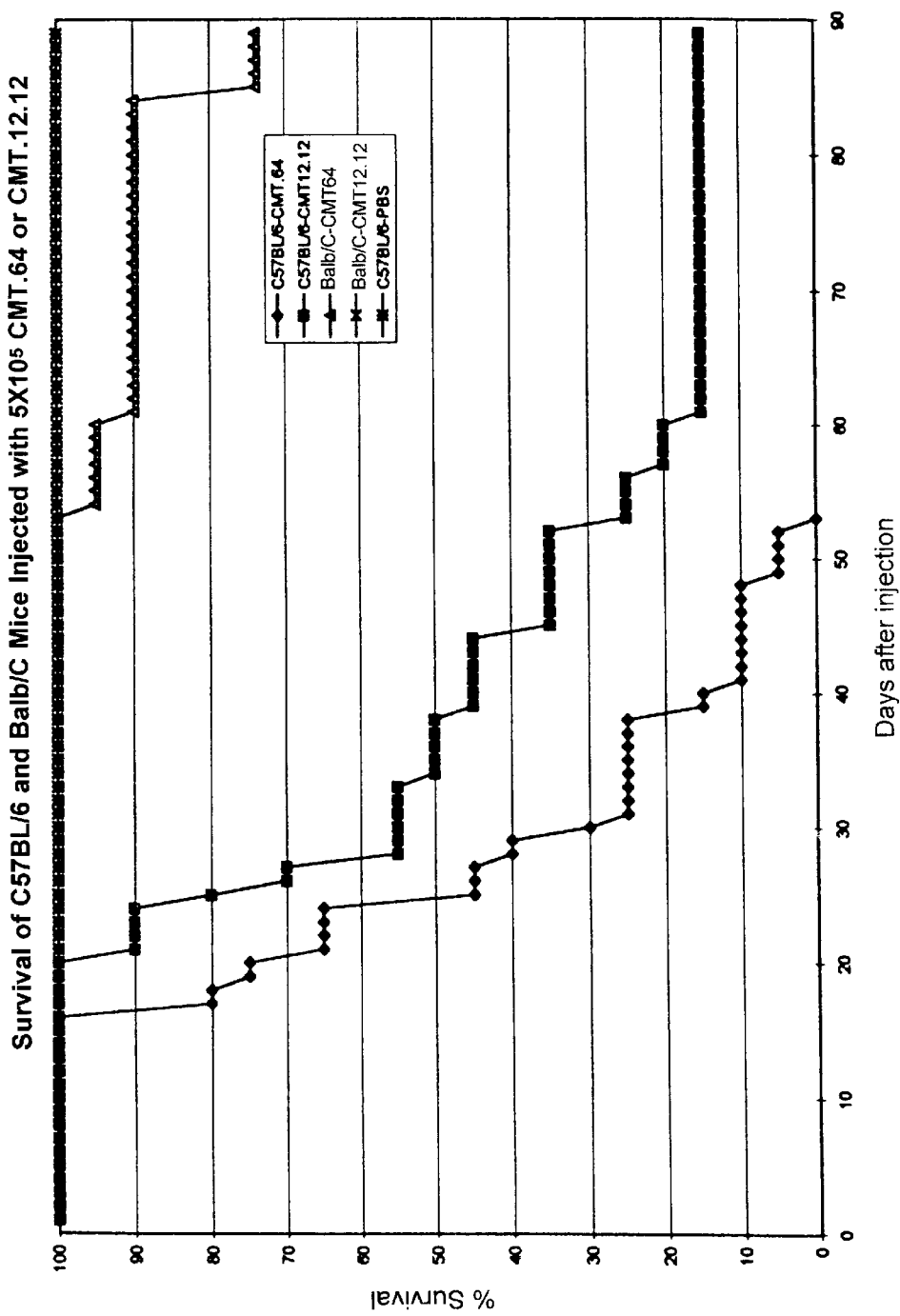

METHOD OF ENHANCING EXPRESSION OF MHC CLASS I MOLECULES BEARING ENDOGENOUS PEPTIDES

This application is a national stage entry of PCT/CA95/00544, filed on Sep. 22, 1995, which claims the benefit of priority to Continuation U.S. application Ser. No. 08/311,442, filed on Sep. 23, 1994, now abandoned.

FIELD OF THE INVENTION

The invention relates generally to a method of enhancing expression of MHC class I molecules bearing endogenous peptides on the surface of a target cell and to a method of augmenting the immune response of a mammal to a tumor cell expressing low or nondetectable levels of MHC class I molecules bearing endogenous peptides. Further, the invention relates to a method of preparing tumor specific T cells which are therapeutically active against tumors.

BACKGROUND OF THE INVENTION

The cytotoxic T lymphocyte (CTL) response is a major component of the immune system, active in immune surveillance and destruction of infected or malignant cells and invading organisms expressing foreign antigens on their surface. The ligand of the antigen-specific T cell receptor is a complex made up of a peptide fragment of a foreign antigen bound to major histocompatibility complex (MHC) molecules. In particular, cytotoxic T lymphocytes recognise peptide bound to MHC Class I molecules.

MHC class I molecules are normally expressed at the cell surface as ternary complexes formed by a heavy chain of 46 kD, a light chain called $\beta_2$-microglobulin ($\beta_2$m) of 12 Kd and a peptide composed of 8–10 amino-acids (van Bleek, G. M. and S. G. Nathenson, Nature 348:213, 1990; Zhang, W. et al., Proc. Natl. Acad. Sci. USA 89:8403, 1992; Matsumura, M. et al., Science 257:927, 1992; and Latron, F., et al., Science 257:964, 1992). Formation of the ternary complex is thought to involve transport into the lumen of the endoplasmic reticulum (ER) of peptides generated by protein degradation in the cytoplasm (Nuchtern, J. G. et al., Nature 339:223, 1989; Yewdell, J. W. and J. R. Bennink, Science 244:1072, 1989; and Cox, J. H. et al., Science 247:715, 1990). The study of mutant cell lines selected for their low expression of MHC class I molecules at the cell surface has provided insights into the molecular events required for antigen processing. These studies have allowed the identification of two genes located in the MHC region which encode proteins of the ATP binding cassette (ABC) family. These genes, called TAP-1 and TAP-2, have been implicated in transport of peptides from the cytoplasm to the lumen of the ER (Deverson, E. V. et al., Nature 348:738, 1990; Trowsdale, J. et al., Nature 348:741, 1990; Spies, T. et al., Nature 348:744, 1990; Monaco, J. J. et al., Science 250:1723, 1990; Spies, T. and R. DeMars, Nature 351:323, 1991; Bahram, S. et al., Proc. Natl. Acad. Sci. USA 88:1009.4, 1991; Spies, T. et al., Nature 355:644, 1992; Kelly, A. et al., Nature 355:641, 1992; Powis, S. H. et al., Proc. Natl. Acad. Sci. USA 89:1463, 1992; and Colonna, M. et al., Proc. Natl. Acad. Sci. USA 89:3932, 1992). Two other MHC linked genes, LMP-2 and -7 (Monaco, J. J. and McDevitt, 1982, Proc. Natl. Acad. Sci. USA 79:3001), are components of the proteasome, a cytoplasmic multicatalytic protease complex, which is likely responsible for some aspects of protein degradation for antigen processing (Ortiz-Navarette, V. et al., Nature 353:662, 1991; Brown, M. G. et al., Nature 353:355, 1991; Glynne, R. et al., Nature 353:357, 1991; Martinez, C. K. and J. J. Monaco, Nature 353:664, 1991; Kelly, A. et al., Nature 353:667, 1991; Yang, Y. et al., Proc. Natl. Acad. Sci. USA 89:4928, 1992; Goldberg, A. L. and K. L. Rock, Nature 357:375, 1992).

The mouse mutant lymphoma cell line RMA-S expresses low levels of class I molecules at the cell surface compared to the wild type RMA cells (Ljunggren, H.-G. et al., J. Immunol. 142:2911, 1989; and Townsend, A. et al., Nature 340:443, 1989). Influenza virus infected RMA-S cells present influenza peptides in the context of $D^b$ molecules inefficiently and are only weakly recognized by specific CTL (Townsend, A. et al., Nature 340:443, 1989). Transfection with the putative transporter gene, TAP-2, complements this deficiency (Powis, S. J. et al., Nature 354:528, 1991; and Attaya, M. et al., Nature 355:647, 1992). The endogenous TAP-2 gene of RMA-S cells was shown to contain a point mutation which introduces a stop translation codon resulting in an incomplete and defective TAP-2 protein (Yang, Y. et al., J. Biol. Chem. 267:11669, 1992). Despite the defective TAP-2 protein in RMA-S cells, antigenic peptides from vesicular stomatitis virus (VSV) bypass the defect and are presented to specific CTL by $K^b$ molecules in RMA-S cells (Esquivel, F., et al., J. Exp. Med. 175:163, 1992; and Hosken, N. A. and M. J. Bevan, J. Exp. Med. 175:719, 1992). The VSV-nucleocapsid (N) peptide, VSV-N 52–59, has been shown to be the major peptide presented by $K^b$ molecules on VSV infected cells (van Bleek, G. M. and S. G. Nathenson, Nature 348:213, 1990). The presence of the wild-type TAP-1 protein in RMA-S cells may be sufficient for translocation of the VSV-N 52–59 peptide to the ER lumen (Powis, S. J. et al., Nature 354:528, 1991; Attaya, M. et al., Nature 355:647, 1992; and Yang, Y. et al., J. Biol. Chem. 267:11669, 1992). Alternatively, the VSV-N 52–59 peptide may not need a functional transporter for transport into the lumen of the ER. Expression of minigene-encoded viral peptide epitopes in T2 cells (Zweerink, H. J. et al., J. Immunol. 150:1763, 1993) and in-vitro translation and translocation using microsomes from T2 cells (Levy, F. et al., Cell 67:265, 1991) support this contention.

A separate class of antigen processing variants are those in which the assembly and the surface expression of MHC class I molecules are entirely inducible by IFN-$\gamma$ (Klar, D. and G. J. Hämmerling, EMBO J. 8:475, 1989). For example in the small lung carcinoma cell line, CMT.64, recognition by influenza virus specific CTL does not take place unless induced with IFN-$\gamma$ (Sibille, C. et al., Eur. J. Immunol. 22:433, 1992). The very low amount of all proteasome components present in uninduced CMT.64 cells is presumed to be responsible for their phenotype (Ortiz-Navarette, V. et al., Nature 353:662, 1991). Exogenous influenza peptides can bind to $D^b$ molecules on CMT.64 cells and complement recognition by influenza specific CTL (Sibille, C. et al., Eur. J. Immunol. 22:433, 1992). In addition, it has been found that the $\beta_2$m and the VSV-N 52–59 peptides added exogenously to these cells complement recognition by VSV specific CTL restricted to $K^b$ (Jefferies W. A. et al., 1993, J. Immunol. 151:2974). The amount of $\beta$2m and of heavy chains synthesized in these cells may limit the amount of MHC class I expression on the cell surface (Jefferies et al, supra, 1993). A dysfunction of the putative peptide transporters and/or in the generation of the peptide may be responsible for the CMT.64 phenotype which may represent a mechanism to downregulate MHC class I expression, a feature common to many carcinomas.

Restifo, N. R. et al. (J. Exp. Med. 177:265–272, 1993) studied the antigen processing efficiency of 26 different human tumor lines using a recombinant vaccinia virus (Vac) to transiently express the $K^d$ molecule. Three cell lines, all human small cell lung carcinoma, consistently failed to process endogenously synthesized proteins for presentation to $K^d$-restricted, Vac-specific T cells. Pulse-chase experiments showed that MHC class I molecules were not transported by the cell lines from the endoplasmic reticulum (ER) to the cell surface. Northern blot analysis of the cells revealed low to nondetectable levels of mRNAs for MHC-encoded proteasome components LMP-7 and LMP-2 as well as the putative peptide transporters TAP-1 and TAP-2.

SUMMARY OF THE INVENTION

The present inventors have surprisingly found that, despite the multiple antigen processing deficiencies in CMT.64 cells, TAP-1 transfected into the cells, alone was sufficient to induce CTL recognition of VSV infected cells in the absence of IFN-γ induction. Importantly, TAP-1 was shown to function independently of TAP-2 in peptide transport, as the transfected cells remained negative for TAP-2 expression. It was also demonstrated that TAP-1 alone delivered specific peptides to the site of MHC assembly, permitting stable complexes to form with resultant transport and expression at the cell surface to permit immune surveillance by cytotoxic T lymphocytes (CTL).

Further, it was demonstrated that some peptides are translocated in the ER by TAP-2 alone. For example it was shown that TAP-2 alone in the absence of TAP-1, is sufficient to enhance processing and presentation of the influenza NP366–374 peptide.

The present inventors have importantly shown that mice injected with high loads of CMT.64 cells transfected with TAP-1 and TAP-2 show increased survival rates and significantly decreased pathology and metastasis compared to mice injected with wild type CMT.64 cells.

The invention therefore contemplates a method for enhancing expression of MHC class I molecules bearing endogenous peptides on the surface of a target cell expressing low or nondetectable levels of MHC class I molecules and expressing low or nondetectable levels of TAP-1 and TAP-2 transporter proteins comprising: introducing into the target cell a nucleic acid molecule comprising a sequence encoding TAP-1 or TAP-2 under control of a suitable promoter, and expressing TAP-1 or TAP-2 in the target cell under suitable conditions thereby enhancing processing and presentation of MHC class I molecules bearing endogenous peptides. Preferably, the target cell is a tumor cell which, additionally has a deficiency in proteasome components, most preferably a small lung cell carcinoma cell. In one embodiment, the processing and presentation of endogenous peptides which have the motif RGYVYQGL (SEQ ID NO: 1), which is restricted to $K^b$ are enhanced by introducing a nucleic acid molecule encoding TAP-1. In a second embodiment, the processing and presentation of endogenous peptides which have the motif ASNENMETM (SEQ ID NO:2), which binds to H-2$D^b$, are enhanced by introducing a nucleic acid molecule encoding TAP-2.

In an embodiment of the method, a nucleic acid molecule comprising a sequence encoding TAP-1 or TAP-2 and a second nucleic acid molecule comprising a sequence encoding an antigenic peptide, preferably a T-cell receptor interactive antigen, under control of a suitable promoter are introduced into the target cell.

The invention also relates to the use of a recombinant viral vector comprising a nucleotide sequence encoding TAP-1 or TAP-2 and a nucleotide sequence encoding an antigenic peptide vector to enhance cell surface expression of an MHC class I molecule bearing endogenous peptides in a tumor cell expressing low or nondetectable levels of MHC class I molecules and expressing low or nondetectable levels of the transporter proteins TAP-1 and TAP-2.

The invention still further provides a method of augmenting the immune response of a mammal to a tumor cell expressing low or nondetectable levels of MHC class I molecules bearing endogenous peptides comprising: introducing a nucleic acid molecule comprising a sequence encoding TAP-1 and/or TAP-2 into the tumor cell under control of a suitable promoter and; expressing TAP-1 and/or TAP-2 in the tumor cell under suitable conditions, thereby enhancing processing and presentation of MHC class I molecules bearing endogenous peptides permitting recognition by the mammal's immune response, particularly recognition by cytolytic T cells.

In an embodiment of the method, the nucleic acid molecule is introduced into the tumor cell in a vaccinia virus. A preferred embodiment comprises introducing an additional nucleic acid molecule into the tumor cell; the additional nucleic acid molecule comprising a sequence encoding an antigenic peptide under control of a suitable promoter and; expressing the antigenic peptide in the tumor cell under suitable conditions, thereby enhancing processing and presentation of MHC class I molecules bearing the antigenic peptide permitting recognition by the mammal's immune response, most preferably, the cytolytic T lymphocyte response. In a particular embodiment, the virus may be used as a vaccine to enhance the immune response to the antigenic peptide.

The invention still further relates to a method of preparing tumor specific T cells which have anti-tumor properties comprising removing tumor cells from a subject; introducing a nucleic acid molecule encoding TAP-1 or TAP-2 under the control of a suitable promoter into the tumor cells; implanting the tumor cells in the subject or a mammal have a reconstituted immune system of the subject; and harvesting tumor specific T cells. The tumor specific T cells may be used as a therapeutic agent in vivo in the subject.

These and other aspects of the present invention will become evident upon reference to the following detailed description and attached drawings. In addition, reference is made herein to various publications, which are hereby incorporated by reference in their entirety.

BRIEF DESCRIPTION OF THE DRAWINGS

FIG. 20 is a graph showing survival of C57Bl/6 and Balb/C mice injected with $5 \times 10^5$ CMT.64 or CMT.12.12 cells.

DETAILED DESCRIPTION OF THE INVENTION

Figure 1A:
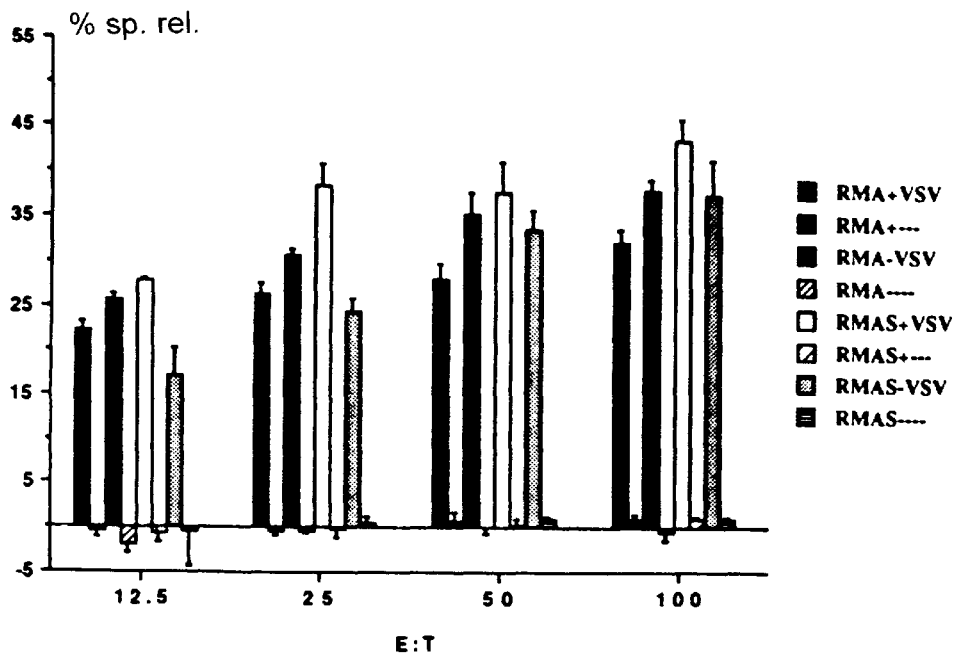
FIG. 1A depicts histograms showing CTL recognition of VSV infected RMA and RMA-S IFN-γ induced (+) or uninduced cells CMT. 64 cells (abbreviated: C)

As hereinbefore mentioned, the present inventors have surprisingly shown that TAP-1 alone, in the absence of TAP-2 is sufficient to enhance processing and presentation of VSV peptides to the intracellular site of MHC assembly, permitting stable MHC class I molecule-endogenous peptide complexes to be formed, transported and expressed at the cell surface. They also demonstrated that TAP-2 alone in the absence of TAP-1, is sufficient to enhance processing and presentation of the influenza NP366–374 peptide.

Accordingly, the present invention provides a method of enhancing expression of MHC class I molecules bearing endogenous peptides on the surface of a target cell expressing low or nondetectable levels of MHC class I molecules and expressing low or nondetectable levels of TAP-1 and TAP-2 transporter proteins comprising: introducing into the target cell a nucleic acid molecule comprising a sequence encoding TAP-1 or TAP-2 under control of a suitable promoter and; expressing TAP-1 or TAP-2 in the target cell under suitable conditions, thereby enhancing processing and presentation of MHC class I molecules bearing endogenous peptides.

Target cells expressing low or non-detectable levels of MHC class I molecules and expressing low or nondetectable levels of TAP-1 and TAP-2 transporter proteins may be selected by methods known in the art. For example, a target cell may be infected with a recombinant viral vector such as VSV, and tested for lysis by VSV specific cytolytic T cells. FACS analysis may also be used to detect MHC class I molecules on the surface of a putative target cell. The biosynthesis and intracellular transport of MHC class I molecules may also be biochemically characterized. For example, endo H which cleaves N-linked oligosaccharides only when they are in the high mannose form characteristic of proteins present in the ER and cis-Golgi complex may be used to measure intracellular transport. Pulse-chase methodology may also be utilized to confirm target cells expressing low levels of MHC class I molecules. The above methods are illustrated in the Examples herein. See also Restifo, N. P. et al, supra, 1993.

Examples of cells which express low levels of MHC class I molecules are tumor cells derived from colon, breast, lung mesothelioma and lung cancers of the small cell histology (See Restifo, N. P., supra 1993).

Cells expressing low or nondetectable levels of TAP-1 and TAP-2 transporter proteins may be detected by assaying for mRNA encoding these proteins, for example using Northern Blot analysis as described in the Examples herein. Examples of cells which express low levels of TAP-1 and TAP-2 are tumor cells derived from lung cancers of the small cell histology.

Target cells may, in addition to expressing low or non-detectable levels of the transporter proteins TAP-1 and TAP-2, express low or nondetectable levels of one or more of the components of the proteasome, for example LMP-7 and LMP-2.

Examples of endogenous peptides whose expression may be enhanced using the methods of the invention include antigens that interact and activate cytolytic T cells for example, viral antigens such as the VSV N52–59 peptide, influenza NP 366–374 and tumor associated antigens. The studies described herein suggest that endogenous peptides with the motif ASNENMETM and bind to $D^b$ are transported by TAP-2, and endogenous peptides with the motif RGYVYQGL and bind to $K^b$ are transported by TAP-1. Therefore enhancing expression of the former endogenous peptides may be achieved following the methods described herein using a nucleic acid molecule containing a sequence encoding TAP-2 and enhancing expression of the latter may be achieved using a nucleic acid molecule containing a sequence encoding TAP-1.

The nucleic acid molecule comprising a sequence encoding TAP-1 under control of a suitable promoter may be readily synthesised using techniques known in the art. A sequence encoding TAP-1 includes a sequence encoding a protein having the amino acid sequence as set out in Trowsdale, J. et al., Nature 348:741, 1990 and International Application No. PCT/US91/06105 published on Mar. 19, 1992. A nucleic acid molecule comprising a sequence encoding TAP-1 may be isolated and sequenced, for example, by synthesizing cDNAs from RNA and using rapid amplification of cDNA ends (RACE, Frohman, et al., 1988) using oligonucleotides specific for TAP-1, and analysing the sequences of the clones obtained following amplification. Oligonucleotides specific for TAP-1 may be identified by comparing the nucleic acid sequence of the nucleic acid molecules of the invention to known sequences of TAP-1. Nucleic acid molecules used in the method of the invention encoding TAP-1 may also be constructed by chemical synthesis and enzymatic ligation reactions using procedures known in the art. The sequence encoding TAP-1 may also be prepared using recombinant DNA methods.

Some of the methods contemplated herein use nucleic acid molecules containing sequences encoding truncated non-functional forms of TAP-1 or TAP-2. Truncated non-functional forms of TAP-1 and TAP-2 may be identified by deleting portions of the TAP-1 or TAP-2 gene to produce fragments. Such fragments should hybridize to the TAP-1 or TAP-2 sequences under stringent hybridization conditions. Stringent hybridization conditions are those which are stringent enough to provide specificity, reduce the number of mismatches and yet are sufficiently flexible to allow formation of stable hybrids at an acceptable rate. Such conditions are known to those skilled in the art and are described, for example, in Sambrook, et al, (1989, Molecular Cloning, A Laboratory Manual, Cold Spring Harbor). The ability of the truncated forms of TAP-1 and TAP-2 to transport endogenous peptides may be determined using the methods described herein.

Nucleic acid molecules having a sequence which codes for TAP-1 or TAP-2 may be incorporated in a known manner into an appropriate expression vector which ensures good expression of the protein or part thereof. Possible expression vectors include but are not limited to cosmids, plasmids, or modified viruses, so long as the vector is compatible with the target cell used.

It is contemplated that the nucleic acid molecules described herein contain the necessary elements for the transcription and translation of the inserted sequence. Suitable transcription and translation elements may be derived from a variety of sources, including bacterial, fungal, viral, mammalian, or insect genes. Selection of appropriate transcription and translation elements is dependent on the target cell chosen as discussed below, and may be readily accomplished by one of ordinary skill in the art. Examples of such elements include: a transcriptional promoter and enhancer or RNA polymerase binding sequence, a ribosomal binding sequence, including a translation initiation signal. Additionally, depending on the host cell chosen and the vector employed, other genetic elements, such as an origin of replication, additional DNA restriction sites, enhancers, and sequences conferring inducibility of transcription may be incorporated into the expression vector. It will also be appreciated that the necessary transcriptional and translation elements may be supplied by the native TAP-1 gene, TAP-2 gene and/or their flanking regions.

The nucleic acid molecules may also contain a reporter gene which facilitates the selection of transformed or transfected host cells. Examples of reporter genes are genes encoding a protein such as β-galactosidase, chloramphenicol acetyltransferase, firefly luciferase, or an immunoglobulin or portion thereof such as the Fc portion of an immunoglobulin preferably IgG. In a preferred embodiment, the reporter gene is lac Z. Transcription of the reporter gene is monitored by changes in the concentration of the reporter protein such as β-galactosidase, chloramphenicol acetyltransferase, or firefly luciferase. This makes it possible to visualize and assay for expression of TAP-1.

Nucleic acid molecules comprising a sequence encoding TAP-1 or TAP-2 can be introduced into target cells via transformation, transfection, infection, electroporation etc. Methods for transforming transfecting, etc. host cells to express foreign DNA are well known in the art (see, e.g., Itakura et al., U.S. Pat. No. 4,704,362; Hinnen et al., PNAS USA 75:1929–1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. Molecular Cloning A Laboratory Manual, 2nd edition, Cold Spring Harbor Laboratory Press, 1989, all of which are incorporated herein by reference).

Suitable expression vectors for directing expression in mammalian cells generally include a promoter, as well as other transcriptional and translational control sequences. Common promoters include SV40, MMTV, metallothionein-1, adenovirus Ela, CMV, immediate early, immunoglobulin heavy chain promoter and enhancer, and RSV-LTR. Protocols for the transfection of mammalian cells are well known to those of ordinary skill in the art.

In a preferred embodiment, the nucleic acid molecule is introduced into the target cell in a viral vector, preferably a vaccinia viral vector, most preferably attenuated. Suitable promoters for use with vaccinia viruses include P7.5 (Cochran, M. A. et al, 1985, *J. Virol.* 54:30), P11 (Bertholet, C. et al, 1985, *Proc. Natl. Acad. Sci. USA* 82:2096), CAE-1 (Patel, D. D. et al, 1988, *Proc. Natl. Acad. Sci. USA* 85:9431).

The nucleic acid molecule may be inserted into a non-essential site of a vaccinia viral vector. Such non-essential sites are well known and are described, for example, in Perkus et al, 1986, *Virology* 152:285; Hruby et al, 1983, *Proc. Natl. Acad. Sci. USA* 80: 3411 and; Weir and Moss, 1983, *J. Virol.* 46:530). Recombinant viruses expressing TAP-1 may be readily identified using techniques known in the art and discussed, for example, in Moss, B, 1992, (Curr. Topics Microbiol. Immunol. 158:25).

In a preferred embodiment, an additional nucleic acid molecule comprising a sequence encoding an antigenic peptide, preferably a pathogenic peptide, under control of a suitable promoter is introduced into the target cell.

As hereinbefore mentioned, the present inventors have demonstrated that TAP-1 or TAP-2 alone can enhance expression of MHC class I molecule-endogenous peptide complexes on the surface of target cells, thereby rendering the target cells susceptible to immune surveillance by CTL.

Accordingly, the present invention provides a method of augmenting the immune response of a mammal to a tumor cell expressing low or nondetectable levels of MHC Class I molecules and expressing low or nondetectable levels of TAP-1 and TAP-2, comprising: introducing a nucleic acid molecule comprising a sequence encoding TAP-1 or TAP-2 into the tumor cell under control of a suitable promoter and; expressing TAP-1 or TAP-2 in the tumor cell under suitable conditions, thereby enhancing processing and presentation of one or more endogenous peptides permitting recognition by the mammal's immune response.

In a preferred embodiment, the method further. comprises: introducing an additional nucleic acid molecule into the tumor cell, said additional nucleic acid molecule comprising a sequence encoding an antigenic peptide under control of a suitable promoter and; expressing the antigenic peptide in the tumor cell under suitable conditions, thereby enhancing presentation and processing of the antigenic peptide permitting recognition by the mammal's immune response.

The invention still further relates to a method of preparing tumor specific T cells which have anti-tumor properties comprising removing tumor cells from a subject; introducing a nucleic acid molecule encoding TAP-1 or TAP-2 under the control of a suitable promoter into the tumor cells; implanting the tumor cells in the subject or a mammal have a reconstituted immune system of the subject; and harvesting tumor specific T cells. It will be appreciated that in an embodiment the nucleic acid molecule may also encode both TAP-1 and TAP-2 or that separate nucleic acid molecules encoding TAP-1 and TAP-2 may be introduced into the tumor cells. The tumor specific T cells may be used as a therapeutic agent in vivo in the subject. Methods such as those described in Restifo, N. P. et al *J. Exp. Med* 175:1423–1431 may be used to prepare specific T cells which anti-tumor properties in vivo using tumor cells transfected with IFN-γ. Adoptive immunotherapy models can be used to confirm the utility of the preparation against established non-modified tumor cells in vivo.

The invention also contemplates that nucleic acid molecules encoding TAP-1 and/or TAP-2 may be incorporated into recombinant viral vector vaccines for use in augmenting the immune response to a pathogen or tumor and for use in treating cancers, in particular metastatic small cell lung carcinomas. Such vaccines are expected to have particularly useful application for mammals, including humans, which are unable to mount an immune response to certain viral or tumor antigens or where their HLA makeup does not permit adequate processing and presentation of the relevant antigenic peptide. For example, for use in persons or for tumor cells lacking in components of the antigen presentation system, such as TAP-1, TAP-2 and proteasome components It will be appreciated that the nucleotide sequences encoding TAP-1 and TAP-2 may be used separately or may be included together, either under the control of separate promoters or under the control of the same promoter.

Recombinant vaccinia virus vaccines may be constructed using techniques known in the art. For example, the pJS5 shuttle vector which contains two early/late compound promoters may be used to express both TAP and the relevant antigen in an infected cell simultaneously. The TAP gene or genes may be cloned behind one promoter and the protein or peptide gene can be cloned behind the second promoter, or in a second vaccine. TAP-1 may be cloned behind one promoter and TAP-2 may be cloned behind a second promoter. The cloned genes may be flanked by the thymidine kinase gene. The pJS5-TAP-antigen vector can be transfected into a vaccinia infected cell so the homologous recombination can occur between the thymidine kinase sequence in both vaccinia and the cloned shuttle vector, resulting in either a recombinant vaccinia virus containing TAP and the antigen, or a recombinant vaccinia virus containing both TAP-1 and TAP-2 which would allow particular peptides to be transported and presented.

The invention also contemplates a method for inhibiting rejection by a recipient animal of a transplanted tissue comprising modifying, eliminating, or masking expression of TAP-1, TAP-2 or both TAP-1 and TAP-2 in cells of said tissue to inhibit endogenous antigen processing and presentation on the surface of cells of said tissue which cause a T-lymphocyte mediated response in said animal. Expression of TAP-1, TAP-2 or TAP-1 and TAP-2 may be modified, eliminated or masked using TAP-1, TAP-2 and/or TAP-1 and TAP-2 antisense. Class I MHC molecules may also be eliminated from the cells of the transplant tissue and truncated forms of TAP-1, TAP-2 and/or TAP-1 and TAP-2 may be used to compete with the functional transporters resulting in down-regulation of expression of TAP-1 and/or TAP-2.

The following examples are offered by way of illustration only, and not by way of limitation.

EXAMPLES

The following materials and methods were utilized in the investigations outlined in Examples 1 to 8.

Animals and Viruses

C57Bl/6 mice were bred at the University of British Columbia breeding facility. Mice were 6–12 weeks old and were maintained in accordance with the guidelines of the Canadian Council on Animal Care. VSV was grown on vero cell monolayers. Vaccinia and a human $\beta_2$m (h$\beta_2$m) vaccinia recombinant were gifts from Dr. J. Yewdell.

Cell Lines and Antibodies

CMT.64 cells (H-$2^b$), were provided by Dr. L. M. Franks (Franks, L. M. et al 1976, Cancer. Res. 36:1049). RMA and RMA-S cells were maintained in DMEM supplemented with 10% heat activated FCS, 20 Mm Hepes, 2 mM glutamine, and antibiotics. The mABS used were as follows: 142–23.3 anti H-2 $K^b$, 28-11-5s anti H-2 $D^b$ ($\alpha$1+$\alpha$2), 28-14-8s anti H-2 $D^b$ ($\alpha$3) and BBM.1 against human $\beta_2$m (Brodsky, F. M. et al, 1979, Eur. *J. Immunol.* 9:536). A rabbit antiserum against h$\beta_2$m (Bikoff, E. K et al, 1991, *Nature* 354:235), against exon-8 of H-2$K^b$ (Williams, D. et al, 1989, *J. Immunol.* 142:2796) and against rat proteasome (Brown, M. G. et al, 1991, *Nature* 353:357) were also used.

Transfection

Transfection of CMT.64 cells with cDNA from rat TAP-1 in the pHb Apr-1-neo expression vector (provided by Dr. G. Butcher) was achieved by lipofection (Lipofectin, Gibco BRL, Gaithersburg, Md.) using 10 μg of DNA. Selection was in 1 mg/ml G418 (Gibco BRL). Positive clones were selected and screened by Northern blotting for expression of the rat TAP-1 gene. The results obtained with a representative clone are reported (See FIG. 9). As negative controls, clones obtained from a vector DNA transfection were analyzed by Northern Blotting. The results obtained with a representative clone are reported (See FIG. 9).

Flow Cytometry Analysis

To determine the cell surface expression of MHC class I molecules fluorescence-activated cell sorter (FACSO) analysis (Becton Dickinson & Co., Mountain View, Calif.) was used. RMA, RMA-S and CMT.64 cells were treated with or without recombinant murine gamma interferon (.IFN-γ) at 150–300 units/ml (Genzyme Cytokine Research Products) for 48 hours. The cells were collected and incubated overnight in medium without FCS, with VSV-N 52–59 peptide (50 μM) and/or h$\beta_2$m (2.5 μg). Peptides were purchased from the University of Victoria, Peptide Synthesis Facility (Victoria, BC, Canada). The cells were subsequently removed from culture, washed, and incubated with 1:50 dilution of 142–23.3 ascites, or 200 μl of cell culture supernatant from 28-11-5s and 28-14-8s cells for 45 min on ice. After two washes, the cells were incubated with 100 μl of 1:20 dilution of goat anti-rabbit, or goat anti-mouse FITC conjugated secondary antibody for another 45 minutes on ice. The samples were then fixed in paraformaldehyde (1.5% in phosphate buffered saline) and analyzed on a FACScan® cell sorter using the FACScan®program (Becton Dickinson & Co.) Values reported in Table 1 are in linear terms representing the average of 5,000 cells. The corrected value (minus the value without first antibodies) is reported.

Cell Labeling, Pulse-Chase Experiments, Immunoprecipitation, Isoelectric Focusing and SDS-PAGE.

Cells were washed in MEM medium without methionine 1 hour before labeling and labeled with 150 μCi/ml of $^{35}$S-methionine for 1 hour or as indicated. For the pulse-chase experiments, cells were labeled 15 minutes and then chased with normal medium containing an excess of cold methionine. Labeled cells were solubilized with 1 ml of 20 Mm Tris-Hcl (pH 7.6) containing 0.12 M NaCl, 4 Mm $MgCl_2$ and 1% Nonidet P-40, phenylmethylsulfonylfluoride (PMSF, a protease inhibitor) was added to a final concentration of 20 µg/ml before use. After 15 min on ice, particulate material was removed by centrifugation. The supernatant was used for immunoprecipitation of labeled antigens. Labeled solubilized antigens were first precleared with 2 µl of normal rabbit serum for 45 min at 4° C. followed by 50 µl of protein A-Sepharose (1:1 in solubilization buffer) for another 45 minutes at 4° C. Protein A-Sepharose was removed by a quick centrifugation. The precleared supernatant was reacted with the appropriate antibody or immune serum for 1 hour at 4° C. 35 µl of protein A-Sepharose was added and incubation continued for a further 30 minutes. After centrifugation the beads were washed twice with 0.2% NP-40 in 10 mM Tris-HCl pH 7.5, 0.15 M NaCl and 2 mM EDTA, once with 0.2% NP40 in 10 Mm Tris-HCl, pH 7.5, 0.5 M NaCl, 2 mM EDTA and finally with 10 mM Tris-HCl pH 7.5. One-dimensional isoelectric focusing was performed as previously described in Celis, J. E. et al (1990, *Electrophoresis* 11:989). SDS-PAGE was carried out as described in Kvist, S. et al, (1982, *Cell* 29:61).

CTL Response Against VSV-Infected, IFN-γ Induced Cells

RMA, RMA-S and CMT.64 cells were treated with or without IFN-γ at 200 units per ml for 48 hours. They were subsequently washed 3× with PBS and treated with VSV at a multiplicity of infection (MOI) of 5 min in 0.5 ml of medium for one hour. The cultures were then incubated in a total of 3 ml of growth medium for an additional 4–8 hours (as indicated), to allow infection to proceed. Single cell suspensions were treated with 100 µCi $^{51}$Cr per $10^6$ cells for 2 hours in RPMI 1640 supplemented with L-glutamine and penicillin/streptomycin in the absence of fetal bovine serum (FBS) and sodium bicarbonate. Alternatively, CMT.64 cells were infected with Vaccinia (V), and/or Vaccinia-b2m (Vb2) at an MOI of 5 for 5 hours followed by superinfection with VSV (MOI,5) for an additional 4 hours. The cells were washed 3× and subsequently incubated at $10^4$ cells per well in 96-well plates with the effector population at ratios of 100 to 12.5. Mock infected cells were used as negative controls. The effector CTL population was generated by immunizing C57Bl/6 mice with VSV at $5\times10^6$–$1\times10^7$ $TCID_{50}$ in the foot pads and ears. On day 5 post immunization the draining lymph nodes (retropharyngeal and popliteal) were harvested and cultures initiated at $4\times10^6$ cells per ml in a total volume of 5 ml in 6-well plates. The culture medium consisted of RPMI-1640 supplemented with $5\times10^{-5}$ M 2-mercaptoethanol (ME), 10% heat inactivated FBS, sodium pyruvate, penicillin, streptomycin, L-glutamine, HEPES, sodium bicarbonate, and 50% NCTC-109. Cultures were incubated for three days at 37° C. and 5% $CO_2$ in the absence of exogenous stimulation. The $^{51}$Cr release was measured by a compugamma counter (model 1282 CS; LKB Instruments, Gaithersburg, Md.) and the specific $^{51}$Cr release calculated as [(experimental–media control)/(total–media control)]×100%. The spontaneous release never exceeded 17% of the maximum release.

RNA Extraction and Northern Analysis

Total cellular RNA was prepared from cell lines using guanidinium isothiocyanate (GITC). Briefly, the cells were lysed in 4 M GITC then centrifuged (130,000 g for 16 hours at 23° C.) through a cushion of cesium chloride. After ethanol precipitation, the purified RNA was resuspended in DEPC-treated $H_2O$. 10 µg of each sample was loaded and separated on a 1 % agarose gel containing 2.2 M formaldehyde. The gel was blotted onto Hybond N (Amersham Corp., Arlington Heights, Ill.) and U/V fixed prior to hybridization. The $^{32}$P-labelled probes used for hybridization were as follows : MTP1 and MTP2 (TAP-1 and -2 respectively, kindly provided by Dr. Geoff Butcher), prepared by random priming, and an oligonucleotide specific for β-actin labelled by terminal transferase. Hybridization was carried out at 42° C. in buffer containing 0.4 M $Na_2HPO_4$, 50% formamide and 7% SDS. Several washes were performed at 42° C. under conditions of increasing stringency and the filter exposed to X-OMAT AR film (Kodak) overnight.

Example 1

Comparison of the Phenotypes of CMT.64 and RMA -S Cells

The small lung carcinoma cell line, CMT.64, was shown to express and assemble MHC class I molecules on the cell surface after IFN-γ treatment (Klar D. and Hammerling, 1989, *EMBO J.* 8:475; Sibille, C. et al, 1992, *Eur. J. Immunol.* 22:433; and Jefferies W. A. et al. 1993, *J. Immunol.* 151:2974). In order to understand the molecular deficiency in antigen processing of CMT.64 cells, the contrasting phenotypes of CMT.64 cells versus RMA-S cells were analyzed. CTL recognition of VSV infected RMA, RMA-S, CMT.64 IFN-γ induced or uninduced cells was investigated generally following the methods outlined in the methodology section herein. More particularly, target cells were treated with or without IFN-γ for 48 hours prior to infection with VSV and the results are shown in FIG. 1. Panel A in FIG. 1 illustrates a representative experiment using RMA and RMA-S cells as targets, whereas panel B is the equivalent experiment with CMT. 64 cells (abbreviated: C). All cells were infected with VSV at an MOI of 10 for 4 hours. IFN-γ treatment is denoted in FIG. 1 with a + sign following the cell line designation. Spontaneous release did not exceed 15%.

Figure 1B:
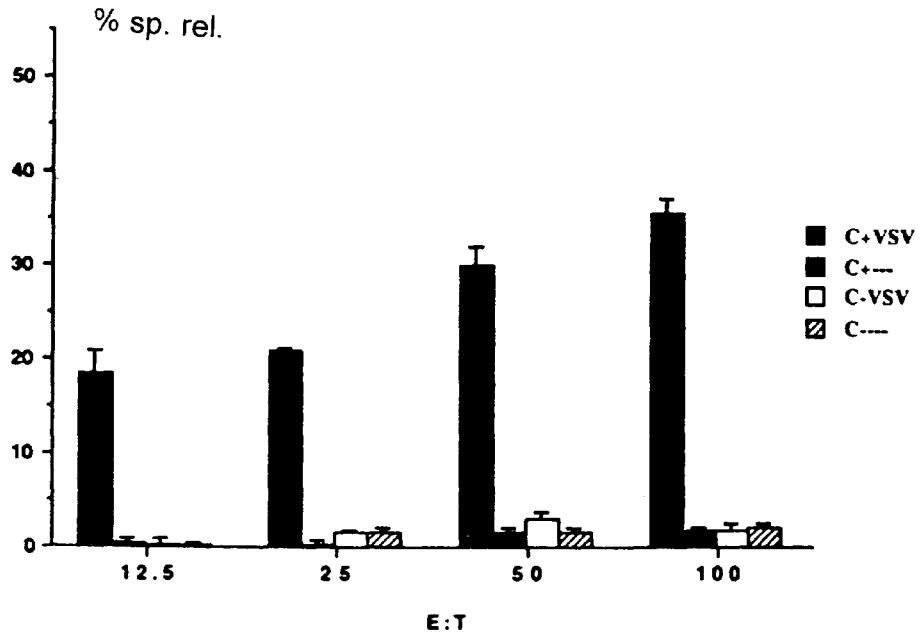
FIG. 1B depicts histograms showing CTL recognition of VSV infected CNT.64 cells (abbreviated: C) IFN-γ induced (+) or uninduced cells.

VSV infected RMA-S cells are recognized as efficiently as the wild-type RMA cells with or without IFN-γ treatment (FIG. 1A), in comparison to VSV infected CMT.64 cells which are not recognized by specific CTL unless induced by IFN-γ (FIG. 1B). It should be noted that RMA-S, RMA and CMT.64 cells are equally permissive to infection with VSV as indicated by the number of infective particles produced following infection measured by a $TCID_{50}$ assay (data not shown). Therefore, uninduced CMT.64 cells have a different or additional deficiency to the functionally defective peptide transporter TAP-2 present in RMA-S cells.

Example 2

The Effect of Exogenous and Endogenous Peptide on the Phenotypes of CMT.64 and RMA-S Cells Previous experiments have demonstrated that treatment of mutant cells with exogenous peptides and/or human $β_2$m can stabilize "empty" class I molecules at the cell surface (Townsend, A., et al. 1989, *Nature* 340:443; Vitiello, A., et al., 1990, *Science* 250:1423; and Ljunggren, H.-G., et al. 1990, *Nature* 346:476). RMA, RMA-S and CMT.64 cells uninduced or induced with IFN-γ were treated overnight with exogenous peptides VSV-N 52–59 at 50 µM in the presence or absence of human $β_2$m. VSV-N 52–59 peptides and $β_2$M synergistically increase the expression of the $K^b$ conformational specific epitope recognized by 142.23.3 mAb (Table I) on RMA and RMA-S cells. VSV-N 52–59 peptides specifically affect the stability and the conformation of the $K^b$ molecules and have no effect on $D^b$ molecules. Human $β_2$m binds to $K^b$ and $D^b$ molecules, which is detected by BBM.1 (anti-human $β_2$m mAb), and appears to stabilize heavy chains before they can disassemble at the cell surface. A stabilizing effect was not seen after CMT.64 treatment with peptides or $\beta_2$m alone. Additional treatment of CMT.64 cells with IFN-$\gamma$ was required for high expression of $K^b$ and $D^b$ conformation specific epitopes on the cell surface (Table I). Therefore, CMT.64 cells express much lower amounts of 'empty' class I molecules at the cell surface than RMA-S cells.

Figure 2:
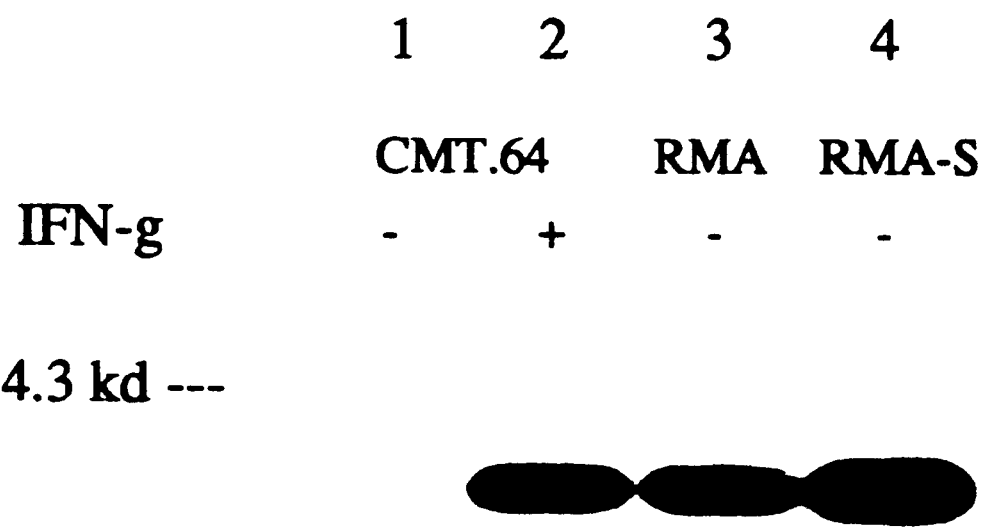
FIG. 2 is an autoradiogram showing the amount of $β_2$m synthesized in RMA, RMA-S and CMT.64 IFN-γ induced (+) or uninduced (−) cells.

Earlier work has shown that the presence of $\beta_2$m and peptides within the lumen of the ER is necessary for efficient assembly and cell surface expression of MHC class I molecules (Rock, K.,et al., 1991, *Cell* 65:611). FIG. 2 shows the amount of $\beta_2$m synthesized in RMA, RMA-S and CMT.64 IFN-$\gamma$ induced or uninduced cells. Cells were labeled for 2 hours with $^{35}$S-methionine lysed, immunoprecipitated with a rabbit anti-h$\beta_2$m serum, and analyzed by SDS-PAGE. Radioactive proteins were detected after 6 hours exposure to a XAR film. CMT.64 cells treated (+) or not (−) with IFN-$\gamma$, RMA and RMA-S cells were used (FIG. 2). The migration of the molecular weight marker is indicated on the left of FIG. 2.

As illustrated in FIG. 2, CMT.64 cells express a low amount of endogenous $\beta_2$m (FIG. 2, lane 1). IFN-$\gamma$ induced CMT.64 cells express a much higher amount of $\beta_2$m, which is comparable to the level expressed in RMA and RMA-S cells (FIG. 2, lanes 2–4).

Figure 3:
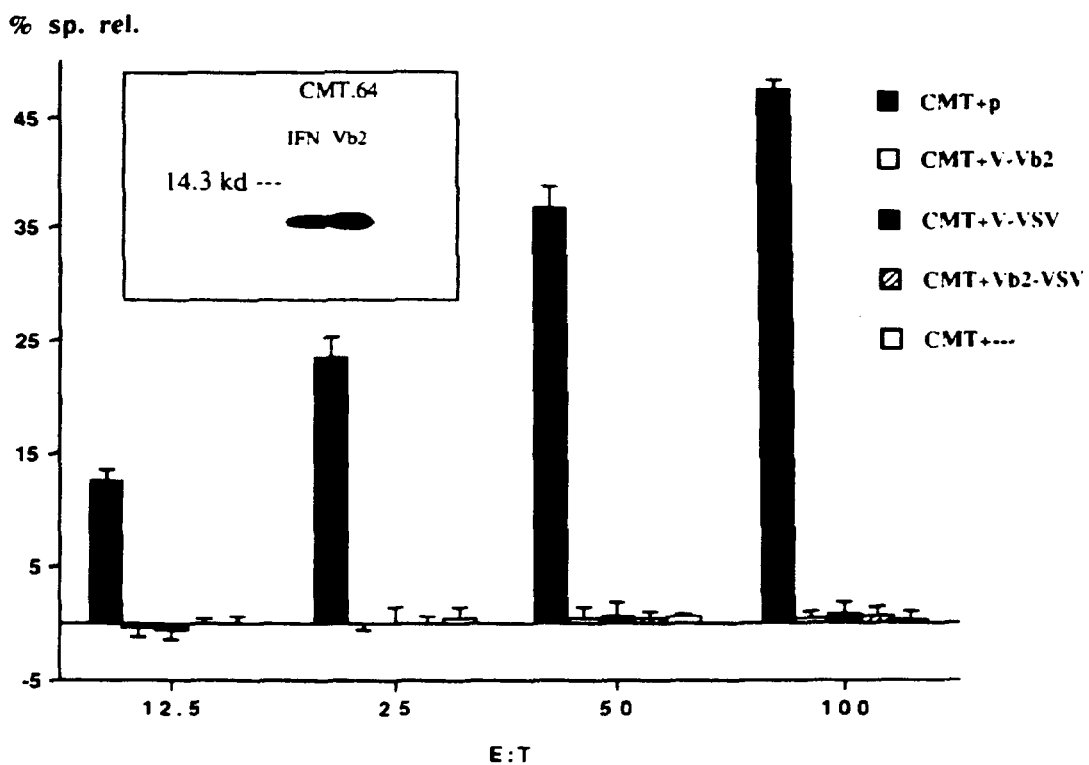
FIG. 3 is a histogram showing the effect of $β_2$m on the CTL response against CMT.64 cells superinfected with Vaccinia and Vaccinia-$β_2$m recombinant (V-Vb2), Vaccinia and VSV (V-VSV), or Vaccinia-$β_2$m and VSV (Vb2-VSV), the insert shows the level of $β_2$m synthesized after immunoprecipitation with the anti-h$β_2$m rabbit serum.

To investigate the effect of $\beta_2$m in CMT.64 cells, a recombinant vaccinia virus was used to increase the amount of endogenous pm. The effect of $\beta_2$m on the CTL response against CMT.64 cells is shown in FIG. 3. Infected CMT.64 cells were superinfected with Vaccinia and Vaccinia-$\beta_2$m recombinant (V-Vb2), Vaccinia and VSV (V-VSV), or Vaccinia-$\beta_2$m and VSV (Vb2-VSV) in FBS free media (MOI 3) for up to an additional 12 hours. In the inset in FIG. 3, the level of $\beta_2$M synthesized is shown after immunoprecipitation with the anti-h$\beta_2$m rabbit serum. CMT.64 cells treated with peptide VSV-N52–59 at 500 pM for 2 hours (CMT+p) was used as the positive control, whereas mock treated CMT.64 cells (CMT+---) were used as the negative control. Radioactivity released is the average of quadruplicate wells. Spontaneous release did not exceed 16%.

As illustrated in FIG. 3, elevating the amount of $\beta_2$m synthesized using a recombinant vaccinia virus did not restore CTL recognition of VSV infected CMT.64 cells. Therefore, increasing expression of $\beta_2$m does not induce presentation of VSV-N peptides in the context of $K^b$ molecules. The CMT.64 antigen processing phenotype is not caused by the low amount of endogenous $\beta_2$m.

Example 3
Intracellular Transport of MHC Class I Molecules $D^b$ and $K^b$

Figure 4:
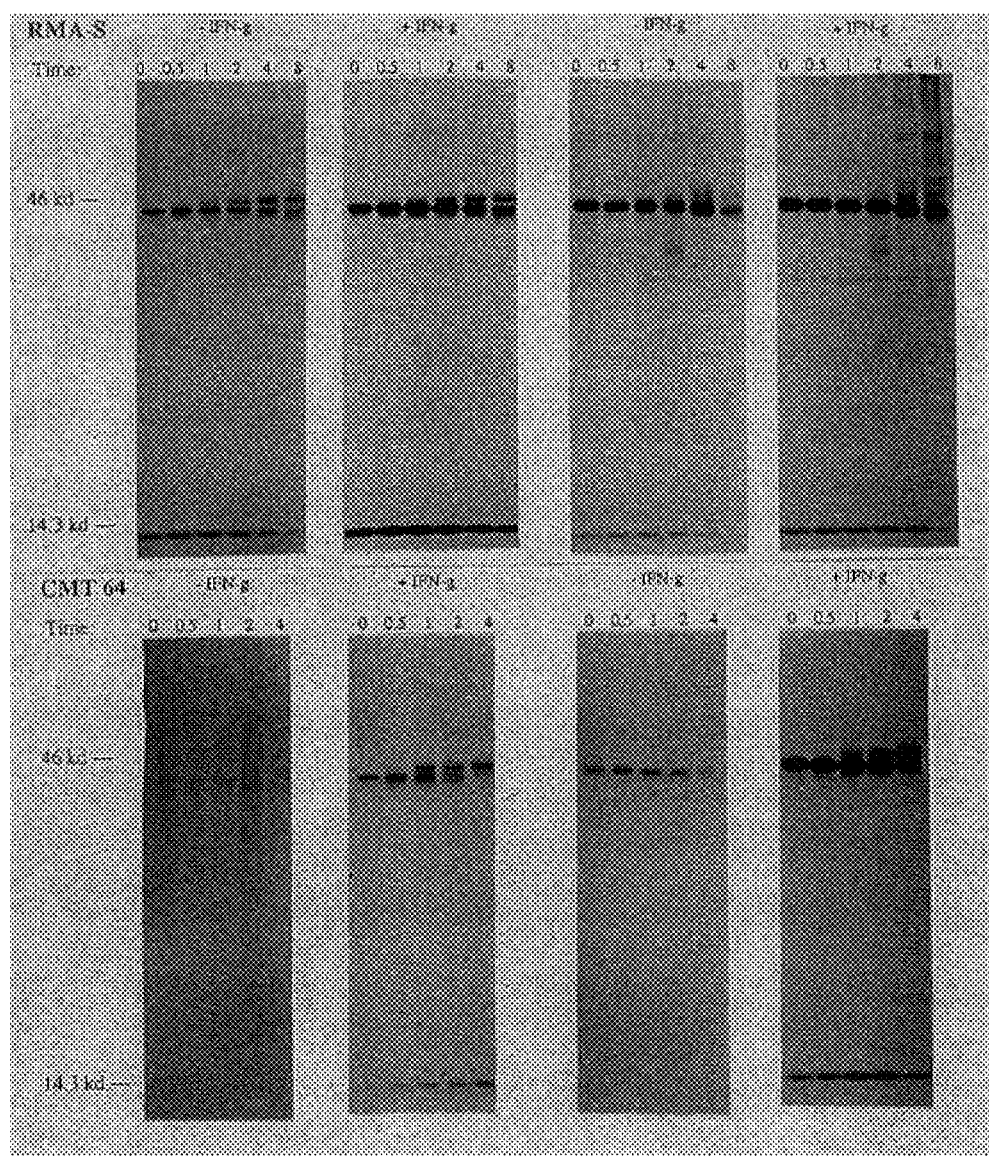
FIG. 4 depicts autoradiograms showing the intracellular transport of MHC class I molecules, $D^b$ and $K^b$.

The transport of $K^b$ and $D^b$ molecules was examined after a pulse-chase labelling of CMT.64, RMA and RMA-S cells and SDS-PAGE analysis of the immunoprecipitated material (for $K^b$, 142.23.3 mAb was used and for $D^b$, 28-14-8s an $\alpha$3 specific mAb was used). Intracellular transport of MHC class I molecules, $D^b$ and $K^b$ is shown in FIG. 4. Cells were labelled with $^{35}$S-methionine and chased in an excess of cold methionine for the times indicated in hours at the top of FIG. 4. Solubilized antigens were immunoprecipitated with 142.23.3 mAbs for $K^b$ or 28-14-8s 5 mAbs for $D^b$. Treatments are indicated on top and the migration of the molecular weight markers is indicated on the left of FIG. 15. Coimmunoprecipitation of the heavy chains (46kD) and $\beta_2$m (12 kD) can be seen for all cells except for CMT.64 uninduced cells. Radioactive proteins were detected after 8 days exposure for RMA-S cells and 4 days for RMA and CMT.64 cells to a XAR film.

Despite a similar amount of $K^b$ molecules synthesized in RMA and RMA-S cells (FIG. 4, 0 hour chase time), only low amounts of $K^b$ are processed to a higher mol.weight form indicative of the level of transport which accounts for the surface expression of $K^b$ in RMA-S cells. The processed form is resistant to endoglycosidase H digestion (data not shown) indicating transport out of the ER. The observation that much more $\beta_2$m was immunoprecipitated with $K^b$ molecules than with $D^b$ molecules in RMA-S cells (FIG. 4) may indicate that the mAb 142.23.3 only recognizes the assembled form, heavy and light chains of $K^b$ molecules, whereas the mAb 28-14-8s recognizes the $\alpha$3 region of $D^b$ molecules. The presence of a functional TAP-1 protein in RMA-S cells (Yang, Y. et al., 1992, *J. Biol. Chem.* 267:11669) may be sufficient to enable some peptides to cross the ER membrane and bind a small number of $K^b$ molecules allowing them to go to the cell surface. Also, peptides with lower affinity for $K^b$ molecules may bind and aid the molecules to assemble and go to the cell surface where they dissociate. Much fewer mature processed $D^b$ molecules were detected in RMA-S cells after 4 hours chase (FIG. 4). This may indicate a lower affinity of $D^b$ for $\beta_2$m and/or fewer peptides available for $D^b$ binding. In RMA cells, $K^b$ molecules were processed within 1 hour. In comparison, $D^b$ molecules were processed more slowly (2 hours) (FIG. 4). These results are in agreement with the relative transport rate of $K^b$ and $D^b$ in RMA-S cells. IFN-$\gamma$ treatment augments the synthesis of heavy chains causing more $K^b$ and $D^b$ molecules to be transported to the cell surface of RMA and RMA-S cells. The rate of transport of $K^b$ and $D^b$ molecules was not affected by IFN-$\gamma$ treatment in RMA and RMA-S cells. In contrast, no $K^b$ molecules were detected in CMT.64 cells using the 142.23.3 mAb.

Example 4
Intracellular Transport of Free and Assembled Forms of $K^b$ Molecules in Uninduced and IFN-$\gamma$ Induced CMT.64 Cells As discussed above, the 142.23.3 mAb may not recognize the unassembled and peptide free heavy chains of $K^b$ molecules (FIG. 4). In order to address this issue, a rabbit anti-exon 8 serum directed against a conformation independent epitope recognizing a peptide in the cytoplasmic tail of H-2$K^b$ molecules (Williams, D. et al, 1989, *J. Immunol.* 142:2796) was used to detect and follow the processing of $K^b$ molecules in uninduced or IFN-$\gamma$ induced CMT.64 cells.

Figure 5:
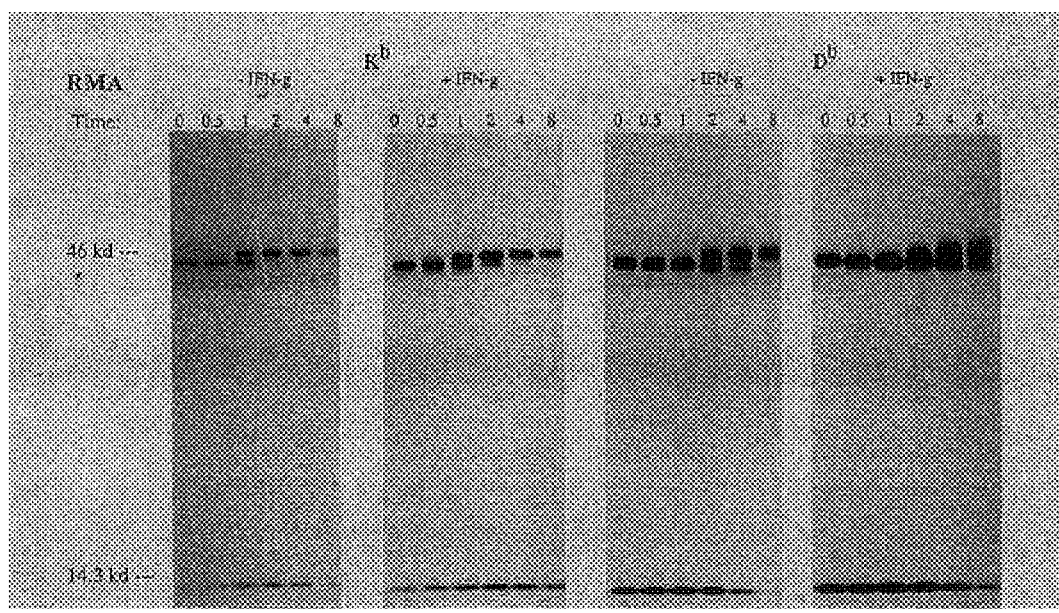
FIG. 5 depicts autoradiograms showing the intracellular transport of free and assembled forms of $K^b$ molecules in uninduced and IFN-γ -induced CMT.64 cells.

Cells were labelled with $^{35}$S-methionine and chased in an excess of cold methionine for the times indicated in hours at the top of FIG. 5. Solubilized antigens were immunoprecipitated with a rabbit anti-exon 8 of H-2$K^b$ serum recognizing the cytoplasmic tail of free and assembled $K^b$ heavy chains as described herein. Treatments are indicated on top and the migration of the molecular weight markers is indicated on the left of FIG. 5. Radioactive proteins were detected after 4 days exposure to a RPN-30 film (Amersham, Corp.).

In uninduced CMT.64 cells, $K^b$ molecules were detectable early after synthesis (FIG. 5, 0 h, 0.5 h and 1 h chase time), but were unstable and mostly degraded after 8 h chase with very few molecules processed to a higher mol. weight (FIG. 5, 8 h chase time). In induced cells, $K^b$ molecules were synthesized in higher amounts and a greater proportion of the molecules were processed to a higher mol. weight (FIG. 5). The decrease in the amount of material immunoprecipitated by this anti-serum during the chase could not be explained. A loss or degradation of the epitope recognized by the anti-serum during transport is possible. Furthermore, $D^b$ molecules are also synthesized and are then degraded or denatured (FIG. 4). In uninduced CMT.64 cells, no processed $D^b$ molecules were detected even after 4 hours chase. Only treatment with IFN-γ results in higher expression, increased transport and increased transport rate of $K^b$ and $D^b$ molecules in CMT.64 cells. Thus, components necessary for the assembly and transport of $K^b$ heavy chains and $β_2$m were induced by IFN-γ in CMT.64 cells, while similar induction did not significantly alter the transport of $D^b$ and $K^b$ in RMA or RMA-S cells. This indicates that CMT.64 cells are likely deficient in components necessary for MHC class I assembly which differ from the TAP-2 defect in RMA-S cells.

Example 5
VSV-N 52–59 Peptide Response in CTL Recognition

Figure 6:
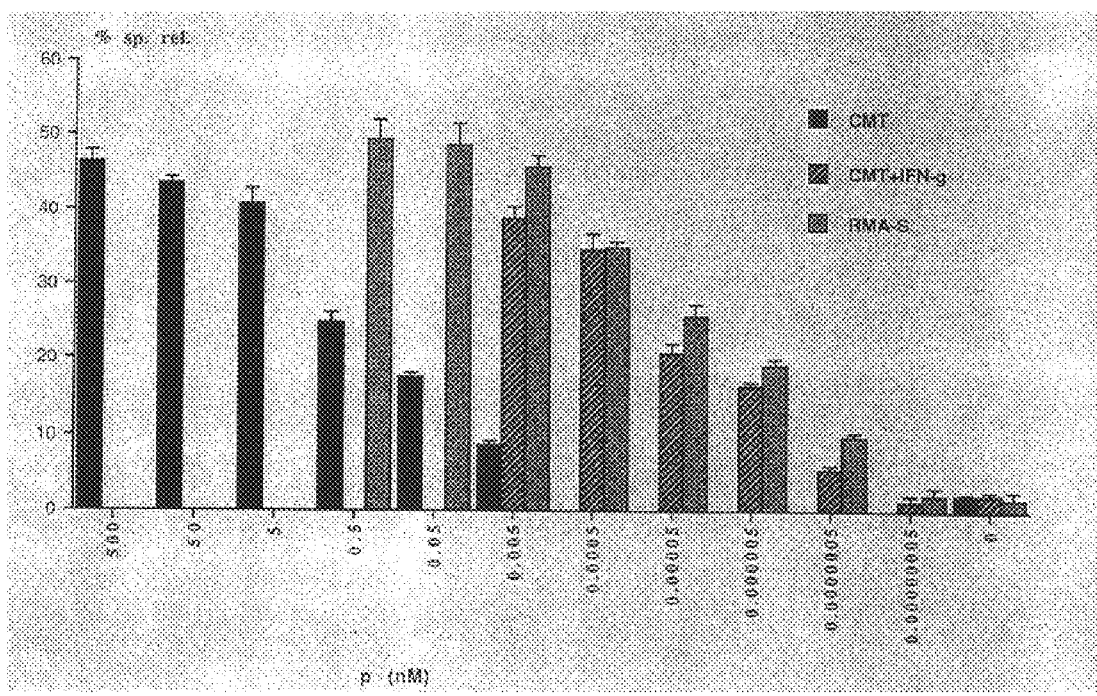
FIG. 6 is a histogram showing VSV-N 52–59 peptide dose response in CTL recognition for CMT.64 cells (CMT), CMT.64+IFN-γ (CMT+IFN-γ) and RMA-S cells (RMA-S)

In order to assay the function of the MHC class I molecules, the CTL recognition of CMT.64 cells IFN-γ induced or uninduced and RMA-S cells treated with exogenous peptides was examined. CMT.64 cells (CMT), CMT.64+IFN-γ (CMT+IFN-γ) and RMA-S cells (RMA-S) were treated with peptide N52–59 at the concentrations indicated in FIG. 6. The radioactivity released by specific CTL recognition and lysis was measured and represented as indicated in materials and methods described above. Radioactivity released, shown in FIG. 6, is the average of quadruplicate wells. Spontaneous release did not exceed 13%.

In a dose dependent manner, RMA-S and CMT.64 IFN-γ treated cells were 10,000 times more sensitive than CMT.64 cells to killing by specific CTL after 2 hours treatment with exogenous peptides (FIG. 6). These results provide evidence for the low expression of peptide receptive MHC class I molecules on the surface of uninduced CMT.64 cells. In the dose-response on RMA-S cells, a maximum of 15,000 peptide molecules per cell were needed to achieve 50% killing by specific CTL, whereas a lower threshold of 150 molecules per cell resulted in the release of 5–10% of $^{51}$Cr. These data may be explained by a high amount of receptive molecules or high affinity of the MHC class I molecules for the peptide on the surface of RMA-S and IFN-γ induced CMT.64 cells. Under the conditions of the present assay, where there is no exogenous $β_2$m, the exogenously added peptides likely stabilize the empty $K^b$ molecules which arrive at the cell surface of RMA-S before they dissociate from β2m (Rock, K. et al, 1991, *Cell* 65:611 and Jefferies W. et al, supra, 1993). The low amount of empty $K^b$ transported in uninduced CMT.64 cells would explain the difference in sensitization to exogenous peptides.

Example 6
Expression of TAP-1 and TAP-2 Genes in CMT.64 and RMA-S Cells

The results shown in FIGS. 2 to 6 indicate that despite its lower expression, $β_2$m alone is not responsible for the lack of antigen presentation in CMT.64 cells. In addition, $K^b$ and $D^b$ molecules are synthesized in these cells but very few are transported to the cell surface where they bind exogenously added peptides. Besides heavy and light chains, peptides are necessary for the efficient assembly of MHC class I molecules in the ER (Spies, T. et al, 1990, *Nature* 348:744; Monaco, J. J. et al, 1990, *Science* 250:1723; Spies, T. and DeMars, R, 1991, *Nature* 351:323 and; Townsend, A. et al, 1989, *Nature* 340:443). The possibility that the absence of components responsible for the generation and transport of these peptides within the ER may be responsible for the CMT.64 phenotype was investigated.

Figure 7:
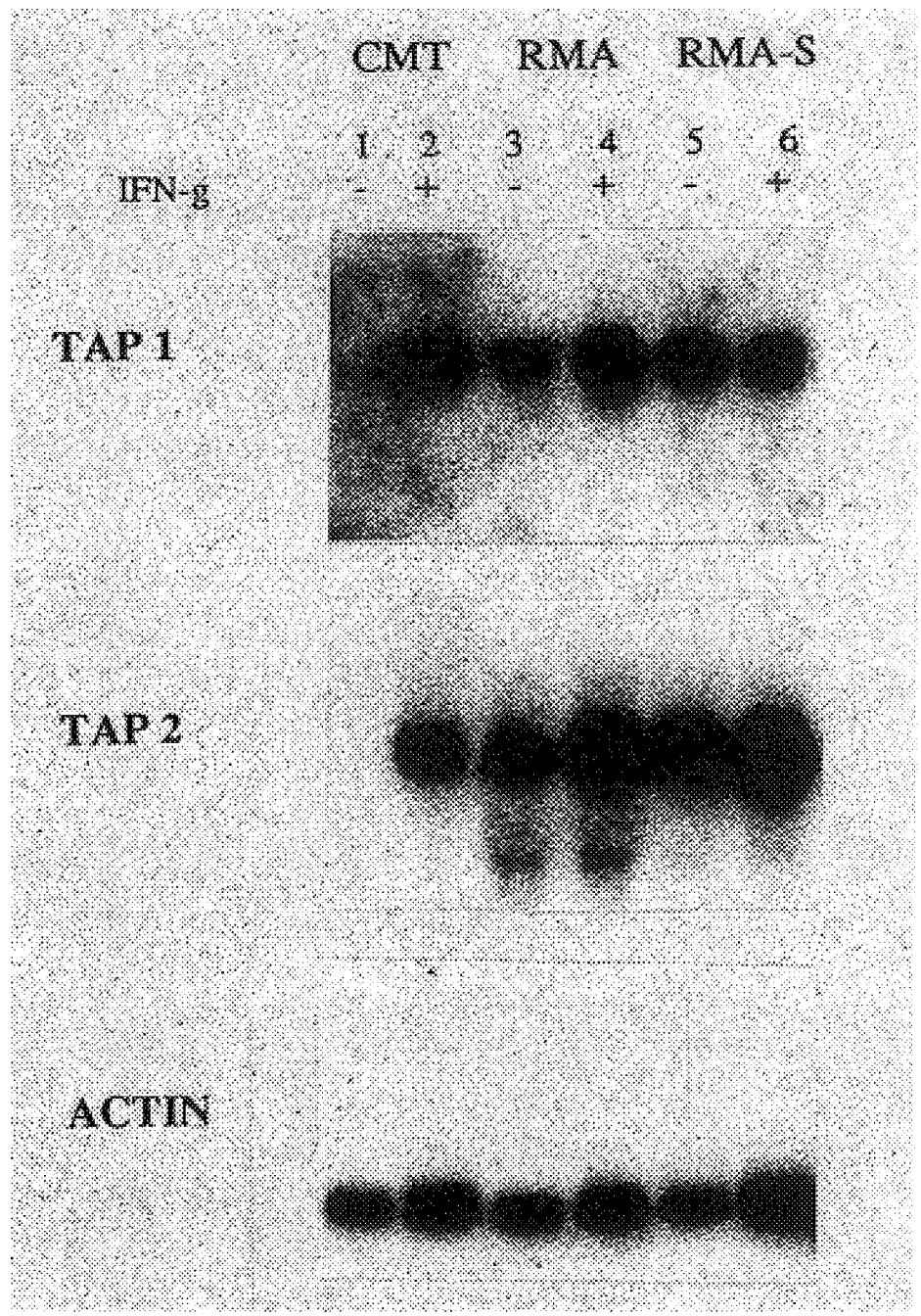
FIG. 7 shows Northern blot analysis of cytoplasmic RNA from RMA, RMA-S, CMT.64 IFN-γ induced and uninduced cells.

A putative peptide transporter, presumed to be composed of a heterodimer of two half-ABC type transporter called TAP-1 and TAP-2, has been implicated in translocating peptides into the ER for MHC class I assembly (Kelly, A. et al, 1992, *Nature* 355:641 and; Powis, S. H. et al, 1992, Proc. Natl. Acad. Sci. USA 89:1463). To characterize the difference of phenotypes between RMA-S and CMT.64 cells, the expression of TAP-1 and TAP-2 genes in these cell lines was examined by Northern blot analysis of total cellular RNA from RMA, RMA-S, CMT.64 IFN-γ induced and uninduced cells (FIG. 7). 10 μg of cytoplasmic RNA from CMT.64, RMA and RMA-S cells IFN-γ induced (+) or uninduced (−) were analyzed and the results are shown in FIG. 7. TAP-1, TAP-2 and β-actin probes were hybridized with the membrane. The radioactivity bound to specific RNA sequences was detected after overnight exposure of the membrane to a XAR film.

In FIG. 7, Northern Blot analysis shows that uninduced CMT.64 cells did not express a detectable amount of TAP-1 and TAP-2 MRNA and that the amount of these mRNAs was highly increased after IFN-γ treatment of these cells. In addition, FIG. 7 shows that no major difference exists between TAP-1 and TAP-2 gene expression in RMA-S and RMA cells, and that IFN-γ treatment only marginally affected TAP-1 and -2 expression in these cells. The amount of actin mRNA gives an indication of the near equal amount of mRNA loaded on the gel for Northern blotting. The IFN-γ inducibility of TAP-1 and -2 has been previously demonstrated in mouse tissues (Gaskin, H. R. et al, 1992, *Science* 256:1826), however this has not been examined in RMA, RMA-S or CMT.64 cells before this study. The results reported here show that the TAP-1 and TAP-2 genes are IFN-γ inducible in CMT.64 cells and to a lesser degree in RMA and RMA-S cells. The absence of TAP-1 and TAP-2 mRNA expression in CMT.64 cells likely causes a lack of antigenic peptides in the ER for binding to and assembly of MHC class I molecules. This results in the non-recognition of VSV-infected CMT.64 cells. In contrast, RMA-S cells express a functional TAP-1 molecule that may aid peptides to cross the ER membrane. This would explain the assembly and transport of MHC class I in RMA-S cells and their CTL recognition after VSV infection. The lack of TAP-1 and TAP-2 in uninduced CMT.64 cells may be one of the factors responsible for the phenotype of CMT.64 cells characterized by the formation of unstable and inefficiently transported MHC class I complexes.

Example 7
Proteasome Components from RMA, RMA-S and CHT.64 IFN-γ Induced or Uninduced Cells Before concluding that TAP deficiencies are the likely or only defects in CMT.64 cells, the presence of proteasome components in these cells was examined. Viral peptides are thought to be generated in the cytoplasm by the proteasome (Ortiz-Navarette, V. et al., *Nature* 353:662, 1991; Brown, M. G. et al., *Nature* 353:355, 1991; Glynne, R. et al., *Nature* 353:357, 1991; Martinez, C. K. and J. J. Monaco, *Nature* 353:664, 1991; Kelly, A. et al., *Nature* 353:667, 1991; Yang, Y. et al., *Prpc. Natl. Acad. Sci. USA* 15 89:4928,1992; and Goldberg, A. L. and K. L. Rock, *Nature* 357:375, 1992) before crossing the ER membrane. The proteasome components are likely key players in antigen processing which could be absent in these cells. A rabbit anti-rat proteasome serum was used which recognizes the mouse proteasome. After immunoprecipitation of the proteasomes, the different component low molecular mass polypeptides (LMP) produced in these mouse cells can be analysed by two dimensional gel electrophoresis.

Figure 8:
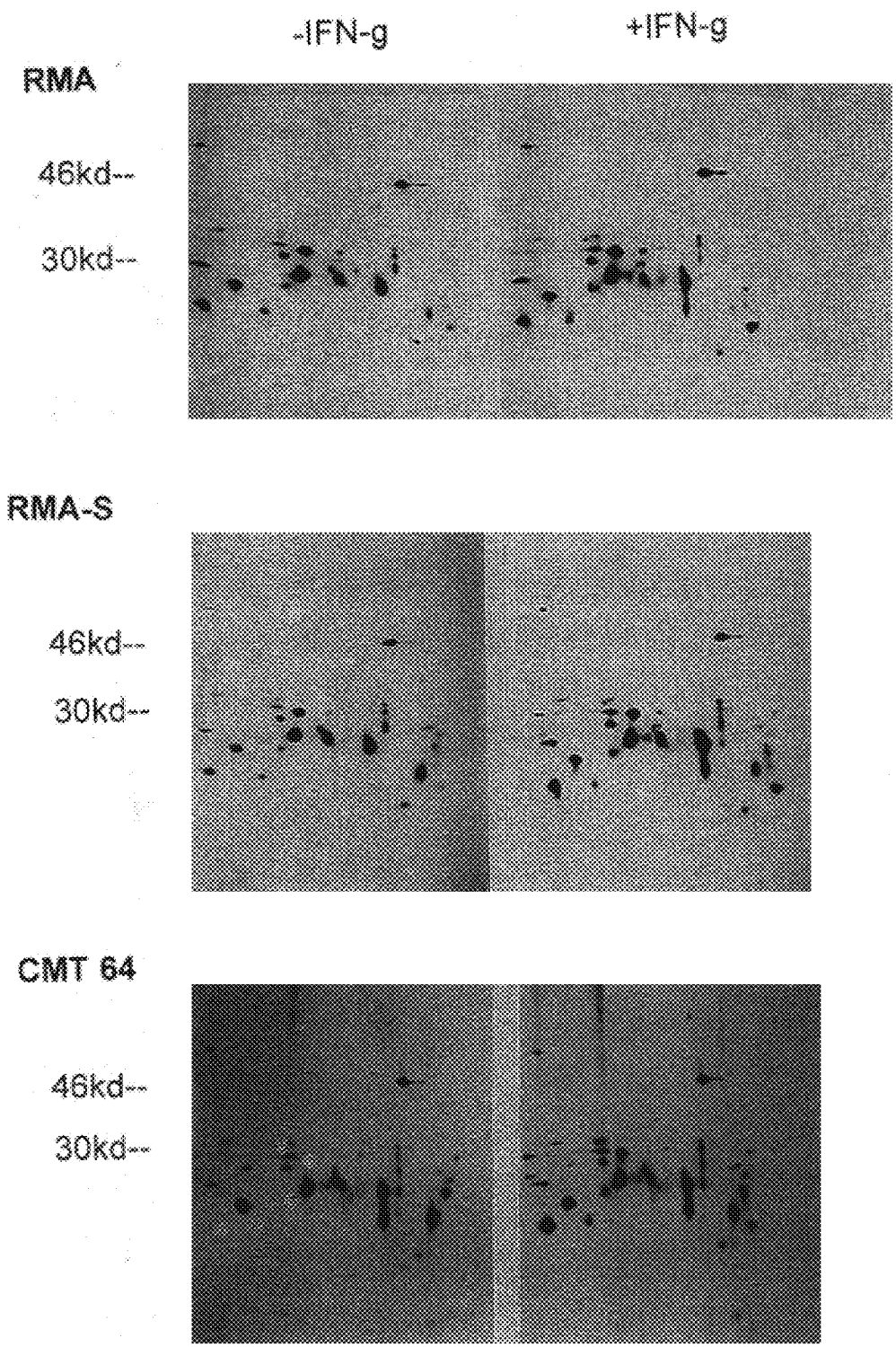
FIG. 8 shows two dimensional gel analysis of proteasome components from RMA, RMA-S and CMT.64 IFN-γ induced or uninduced cells.

Two dimensional gel analysis of proteasome components from RNA, RMA-S and CMT.64 IFN-γ induced or uninduced cells are shown in FIG. 8. Cells were labeled for 2 hours with $^{35}$S-methionine. Solubilized antigens were immunoprecipitated with a rabbit anti-rat proteasome serum and analyzed after isoelectric focusing in a first dimension and 10–15% SDS-PAGE in a second dimension. The radioactive proteins were detected after 10 days exposure to a XAR film. Treatment of the cells is indicated on the top of FIG. 8. The acidic side of the gel is on the right and the basic side is on the left of the gel. The migration of the molecular weight markers is indicated on the left of the gel. The missing proteins are indicated by an arrow and are numbered (FIG. 8). Proteins numbered 1 and 7 correspond to LMP-7 and LMP-2, respectively.

Two dimensional gel analysis of immunoprecipitations revealed that the major components of the proteasome are not affected by IFN-γ treatment of CMT.64 cells but that seven components, including LMP-2 and -7, were missing in uninduced CMT.64 cells. According to the results of others (Fruh, K. et al, 1992, *J. Biol. Chem.* 267:22131), the proteins numbered 1 and 7 in FIG. 8 correspond to LMP-7 and LMP-2, respectively. LMP-2, LMP-7 and five other components of the proteasome were upregulated slightly by IFN-γ in RMA and RMA-S cells and induced from a state of an undetectable expression to a higher detectable level of expression in IFN-γ treated CMT.64 cells (FIG. 8). LMP-7 (FIGS. 8,1) is particularly highly induced in CMT.64 cells treated with IFN-γ. These results contrast the results of others which suggested that CMT.64 express a low level of all proteasome components (Ortiz-Navarette, V. et al, 1991, *Nature* 353:662) and these new results indicate that these induced proteasome components affect the activity of the proteasome and allow the generation of the VSV-N peptides in induced CMT.64 cells. Recent data (Arnold, D. et al., 1992, *Nature* 360:171, and Momburg, F. et al., 1992, *Nature* 360:174) suggest that LMP-2 and -7 may not be necessary for influenza virus antigen presentation in mutant cells transfected with the TAP-1 and -2 genes.

The above results show that IFN-γ treatment in addition to inducing transcription of TAP-1 and TAP-2 genes also upregulates the synthesis of seven components of the proteasomes, including LMP-2 and -7. Others describe that components in addition to LMP-2 and LMP-7 are upregulated in Hela cell proteasomes by IFN-γ treatment (Yang, Y. et al., *Proc. Natl. Acad. Sci. USA* 89:4928,1992; and Früh, K. et al.,*J. Biol. Chem.* 267:22131, 1992). However, as these cells are functionally wild-type, the functional ramification of this regulation has not been addressed. Furthermore, as LMP-2 and LMP-7 are first synthesized as precursor proteins which are cleaved into smaller products (Früh, K. et al., *J. Biol. Chem.* 267:22131, 1992), it is possible that some of the five additional proteins missing from uninduced CMT.64 cells may be precursor proteins of LMP-2 and LMP-7.

Example 8
Recognition of VSV Infected TAP-1 Positive CMT.64 Cells

Consideration of the accumulated data regarding antigen processing in RMA-S and CMT.64 cells leads to the contention that a functional TAP-1 protein homodimer alone may facilitate the transport of the VSV-N 52–59 peptide from the cytosol to the ER lumen where binding to the heavy chains takes place. An alternative explanation is that this peptide does not require a transporter for translocation across the ER membrane but is not generated in the CMT.64 cells. In order to more clearly define the defect affecting the recognition of VSV infected CMT.64 cells by specific CTL, the rat TAP-1 gene was introduced in CMT.64 cells.

Figure 9:
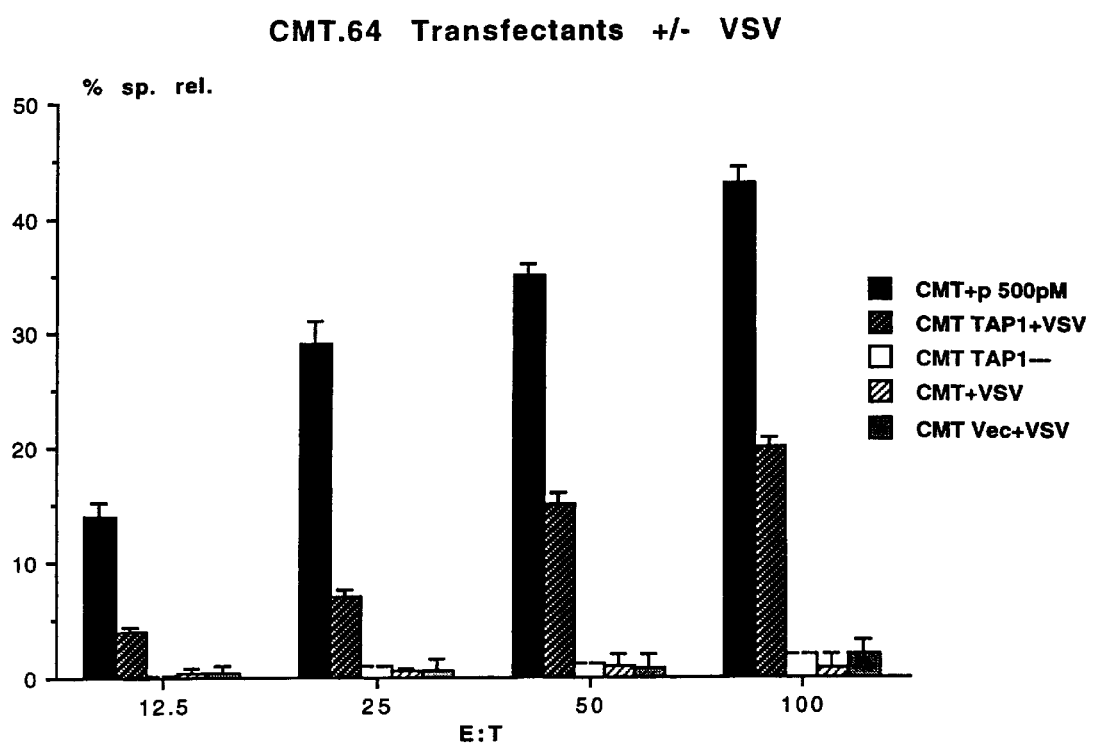
FIG. 9 shows CMT 64 (CMT), and CMT 64 transfected with TAP-1 (CMT TAP 1) infected with or without VSV for 8 hr at MOI of 5, or treated with N52–59 peptide for 2 hr at 500 Pm (50.% dose response)

CMT 64 (CMT), CMT 64 transfected with TAP-1 (CMT TAP 1), and CMT.64 cells transfected with the vector only (CMT Vec) were infected with or without VSV for 8 hours at MOI of 5, or treated with N52–59 peptide for 2 hours at 500 pM (50% dose response). Spontaneous release did not exceed 12%. FIG. 9 shows that VSV infected TAP-1 positive CMT.64 cells were recognized by specific CTL. This result explains the RMA-S phenotype and its apparent "leakiness" regarding VSV presentation (Esquivel, F., et al., *J. Exp. Med.* 175:163, 1992; Hosken, N. A. and M. J. Bevan,*J. Exp. Med.* 175:719, 1992). TAP-1 alone appeared to be sufficient for VSV presentation in RMA-S cells and in transfected CMT.64 cells and may form a homodimer capable of translocation of specific peptides into the lumen of the ER. In addition to transporters, the difference in the RMA-S and CMT.64 phenotype may be explained at one level by the higher amount of viral peptides generated in RMA-S cells. Interestingly it appears that a total repression of the expression of both LMPs and TAPs localized in the same region of class II may be sufficient for avoiding any expression of class I on the cell surface. This may be very important for some cancer cells (Brodsky, F. M. et al., *Eur. J. Immunol.* 9:536, 1979; Restifo, N. P. et al., *J. Exp. Med.* 177:265, 1993; and Bikoff, E. K. et al., *Eur. J. Immunol.* 21:1997, 1991) by providing a method by which tumour cells avoid immunosurveillance.

Example 9
Tap Gene Expression Profiles of CMT.64 and CMT64/R1-4

Figure 10:
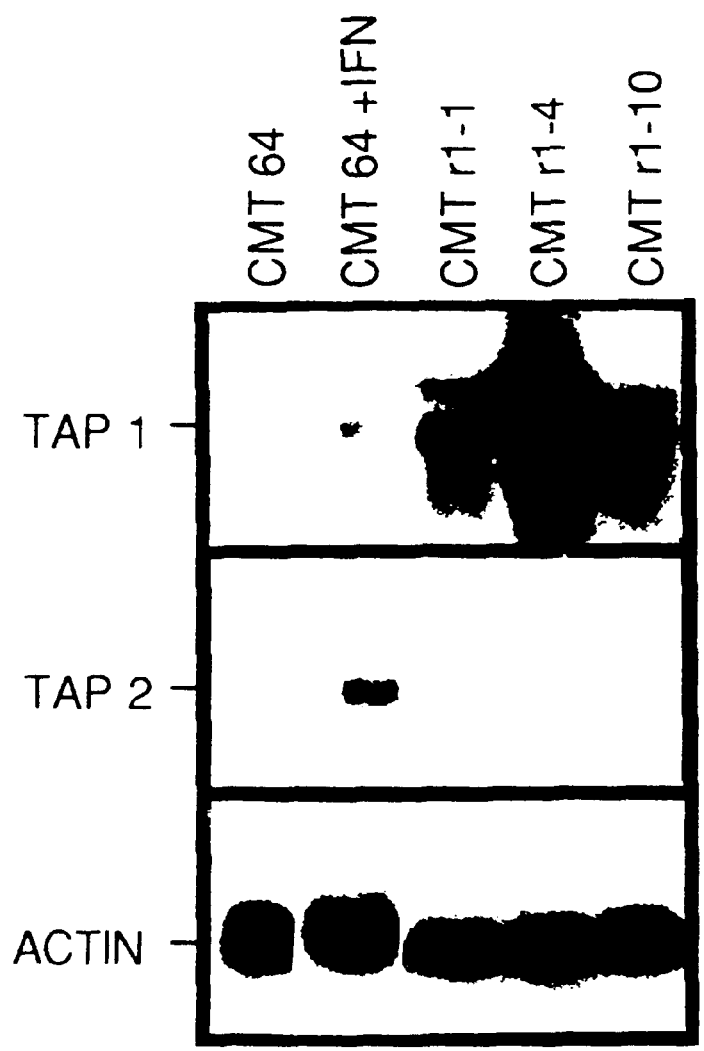
FIG. 10 shows TAP gene expression profiles of CMT.64 and CMT64/r1-4.

In order to investigate the ability of TAP-1 to function independently in peptide transport, the rat TAP-1 cDNA was introduced into the murine small lung carcinoma cell line CMT.64 which does not express endogenous TAP-1 or TAP-2 mRNA (FIG. 10). The endogenous TAP genes, as well as those coding for the putative proteasome components LMP2 and 7, are expressed only after IFN-γ treatment (FIG. 10). Positive transfectants were selected using the neophosphotransferase selection system and constitutive expression of the TAP-1 gene was confirmed by northern blotting.

In particular, transfection of CMT.64 cells with rat cDNA TAP-1 (in the pHb APr-1-neo expression vector as described in Powis, S. J. et al. *Nature* 354, 528–531 (1991)) was achieved by lipofection (Lipofectin, BRL) using 10 μg of DNA. Selection was in 1 mg/ml G418 (Gibco). Total RNA was isolated using guanidine isothiocyanate and electrophoresed on a 1% agarose gel containing 2.2M formaldehyde (10 μg/lane). Blotting and hybridisation with [$^{32}$P]-labelled cDNAs (TAP-1 and 2 ) or oligonucleotide (actin) were carried out as described herein.

Both TAP-1 and 2 mRNA transcripts were absent in uninduced CMT.64 cells but were detected in CMT.64 cells cultured in the presence of 200 units/ml of mouse recombinant IFN-γ for 48 hours (FIG. 10). CMT64/r1-4 expressed high levels of vector-derived TAP-1 mRNA but remained negative for TAP-2. Actin mRNA was used to demonstrate that equal amounts of RNA had been loaded.

Three high expressing clones were selected for subsequent experiments (FIG. 10). Three clones transfected with vector alone were also selected and used as controls in the subsequent experiments.

Example 10
TAP-1 Expression is Sufficient to Increase Levels of $K^b$ and $D^b$ at the Cell Surface of CMT.64 Cells CMT.64 cells also express virtually no surface MHC class I molecules, despite synthesis of both $D^b$ and $K^b$ heavy chains (Jefferies, W. A. et al., supra, 1993). To determine the influence of TAP-1 on surface class I expression, flow cytometry was carried out using antibodies against $D^b$ and $K^b$. In particular, the cells were incubated with or without primary antibody for 1 hour. All incubations were carried out at 4° C. After washing, the cells were incubated with fluorescein isothiocyanate-conjugated goat anti-mouse Ig antibody (20 mg/ml) for an additional hour. Following two rounds of washing, the cells were fixed in 1.5% paraformaldehyde. The fluorescent profiles were obtained by analysing 5,000 cells in a semi-logarithmic plot using a FACScan® programme.

Figure 11:
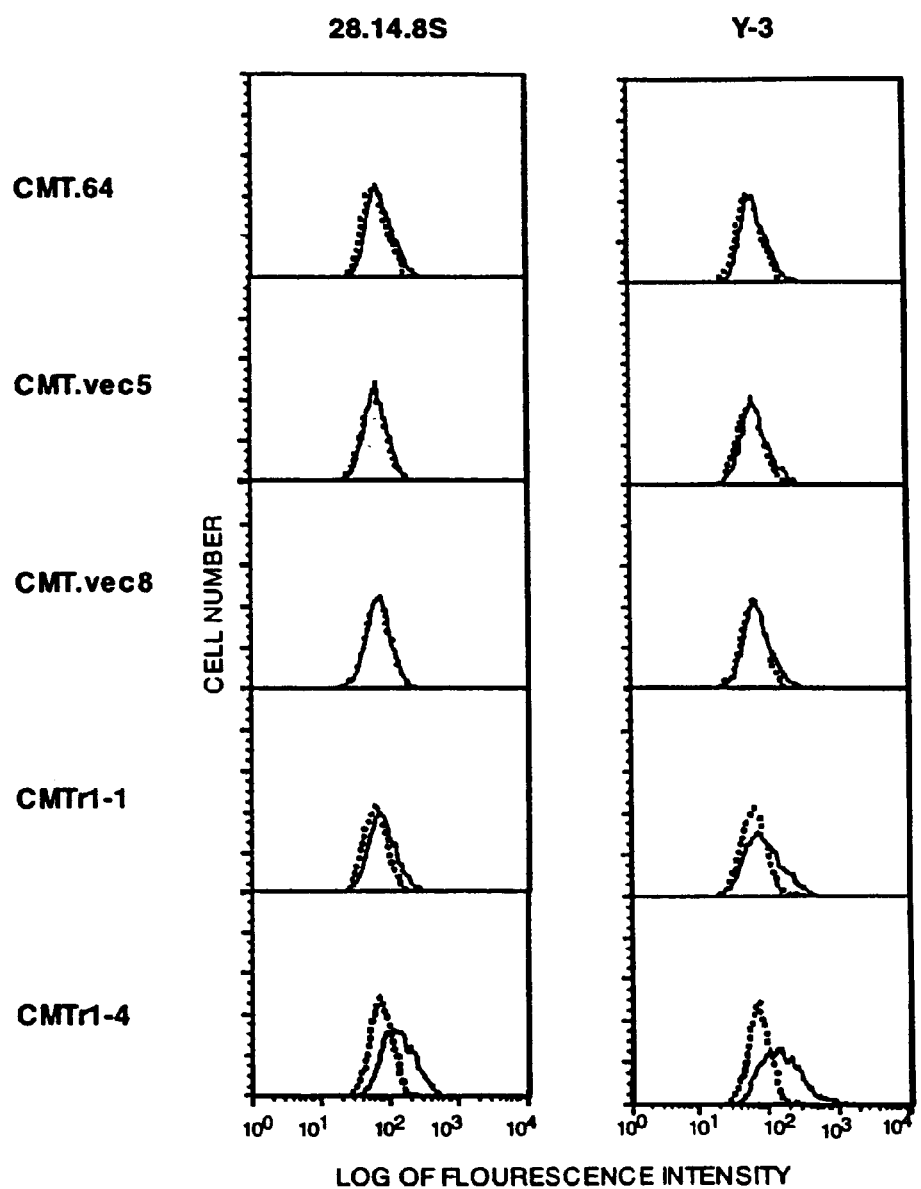
FIG. 11 shows flow cytometric analysis demonstrating that TAP-1 expression is sufficient to increase levels of $K^b$ and $D^b$ at the cell surface of CMT.64 cells.

Flow cytometric analysis demonstrated that TAP-1 expression was sufficient to increase levels of $K^b$ and $D^b$ at the cell surface of CMT.64 cells as shown in FIG. 11. The antibodies 28.14.8s and Y-3 recognise $D^b$ and $K^b$ respectively. In all panels the results obtained with the indicated primary antibody are shown by a solid line. The dotted line represents the values obtained in the absence of a primary antibody. The results shown are representative of three independent experiments.

For both antibodies tested there was a detectable increase in surface expression in the CMT-TAP-1 transfectants compared to CMT.64 and the vector controls, suggesting TAP-1 alone had delivered peptides to the site of MHC assembly, allowing stable complexes to be formed, transported and expressed at the cell surface. The amount of transferrin receptor expressed at the cell surface was unchanged by the transfection of TAP-1, indicating that this was not a general effect on plasma membrane proteins (data not shown) In contrast to other systems where it has not been possible to discount the involvement of an alternative mechanism of peptide transport (Hosken, N. A. & Bevan, M. J. *J. Exp. Med.* 175:719–729 1992; Esquivel, F., Yewdell, J. & Bennink, J. *J. Exp. Med.* 175:163–168, 1992; Zweerink, H. J., et al. *J. Immunol.* 150:1763–1771, 1993), these results clearly demonstrate the ability of TAP-1 to increase surface class I expression in the absence of TAP-2 in CMT.64 cells.

Example 11

Pulse-Chase Analysis of $K^b$ and $D^b$ Molecules from CMT.64 and TAP-1 Transfected CMT.64 Cells Intracellular transport of class I heavy chain to the cell surface is accompanied by processing to a higher molecular weight form by modification of the N-linked glycans during successive exposure to Golgi-specific enzymes. Pulse-chase experiments were therefore performed to determine if such processing was achieved in the CMT-TAP-1 transfectants, as predicted by the increase in surface expression of $K^b$ and $D^b$.

Pulse-chase and immunoprecipitation of $K^b$ and $D^b$ were performed using a 15 minute pulse with $^{35}$S-methionine (Amersham) and immunoprecipitated 28.14.8S (anti-$D^b$) and Y-3 (anti-$K^b$) monoclonal antibodies, following the methods described above. Samples were analysed by SDS-PAGE on 10–15% gels and treated with an amplifying solution. The autoradiogram was developed after 10 days.

Figure 12:
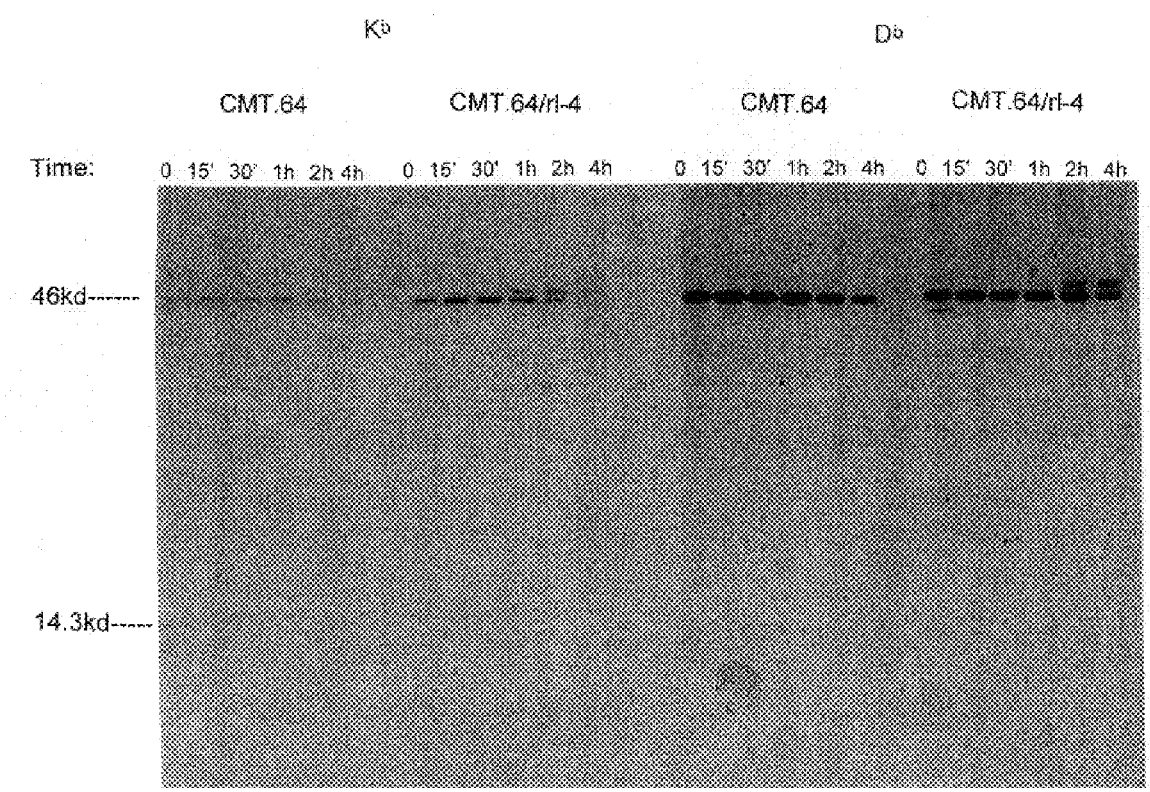
FIG. 12 shows pulse-chase analysis of $K^b$ and $D^b$ molecules from CMT.64 and TAP-1 transfected CMT.64 cells (CMT64/r1-4)

Transport of $K^b$ and $D^b$ molecules to the cell surface occurred in the TAP-1 transfected cells, as indicated by the increase in molecular weight of the heavy chain during oligosaccharide side chain processing (FIG. 12). In untransfected CMT.64 cells no processing was observed (FIG. 12), indicating retention within the endoplasmic reticulum or cis golgi. This was confirmed by sensitivity to endoglycosidase H (data not shown).

In summary, comparison between CMT.64 and CMT64/r1-4 revealed that the presence of TAP-1 was sufficient to allow the processing of $D^b$ and $K^b$ to occur (FIG. 12). In addition, it was determined by endoglycosidase H treatment that the higher molecular weight processed forms of $K^b$ and $D^b$ were resistant to digestion (data not shown). These results further confirm the importance of TAP-1 for the transport and surface expression of MHC class I molecules in these cells.

Example 12

TAP-1 Transfected CMT.64 Cells Efficiently Present Antigen to VSV Specific CTL

In previous studies it was established that CMT.64 cells were unable to present VSV peptides to cytolytic T lymphocytes (CTL) unless pretreated with IFN-γ or incubated directly with a synthetic peptide derived from the VSV N protein (Jefferies, et al. *J. Immunol.* 15 151:2974–2985, 1993). To examine the ability of TAP-1 expression to complement functional antigen processing and presentation, chromium release assays were carried out with VSV-specific CTL using CMT.64 and CMT-TAP-1 and CMT-vector transfectants as targets.

In particular, CMT.64 cells (CMT) and CMT-TAP-1 transfectants were infected with VSV (MOI:2) for 8–10 hours, or treated with Influenza strain A/PR/8/34 for 48 hours (at 300 HA units for RMA, and 500 HA units for CMT.64 and their derivatives). Effector CTL populations were generated by infecting C57bl/6 mice with VSV in the foot pads and ears or 700 HA units of Influenza i.p. VSV CTL were derived from draining lymph nodes as collected on day 5 post immunization and single cell suspensions were cultured at $4 \times 10^6$ cells per ml for 3 days in the absence of any restimulation. Influenza CTL were derived from splenocytes, 4–5 weeks post-immunization, cultured in the presence of influenza infected stimulators for 6 days. The culture medium consisted of a 1:1 ratio of RPMI-1640 and NCTC-109 supplemented with 10% FBS, L-Glutamine, Pen/Strep, and 2 ME. Targets and effectors were mixed and incubated for 4 hours. Mock infected cells (+---) were used as negative controls.The results are expressed as % specific release, as detailed in Jefferies, W. A., Kolaitis, G. & Gabathuler, R. *J. Immunol.* 151, 2974–2985 (1993).

Figure 13:
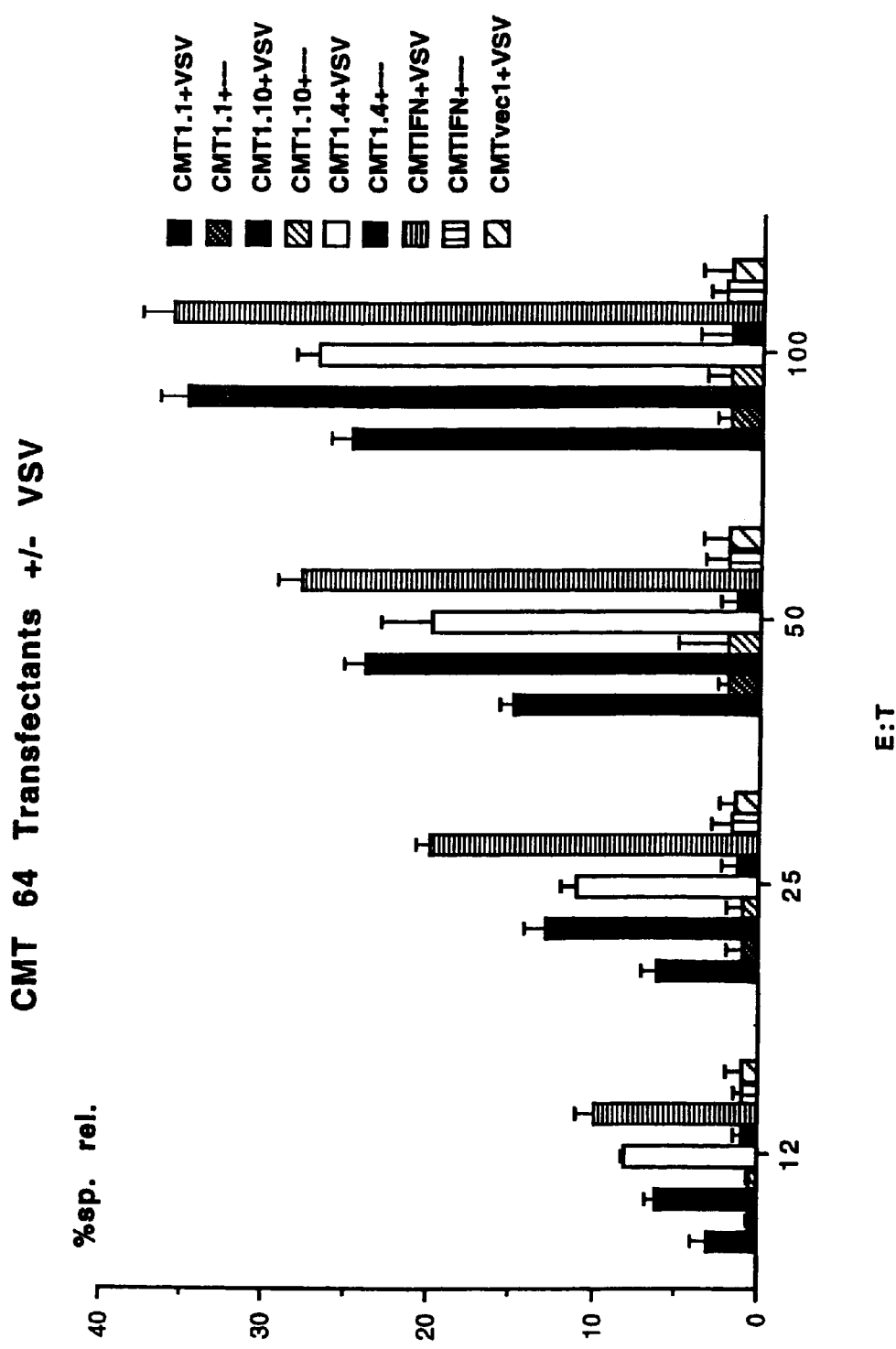
FIG. 13 is a histogram showing that TAP-1 transfected CMT.64 cells (CMT-r1.4) efficiently present antigen to VSV specific CTL.
Figure 17:
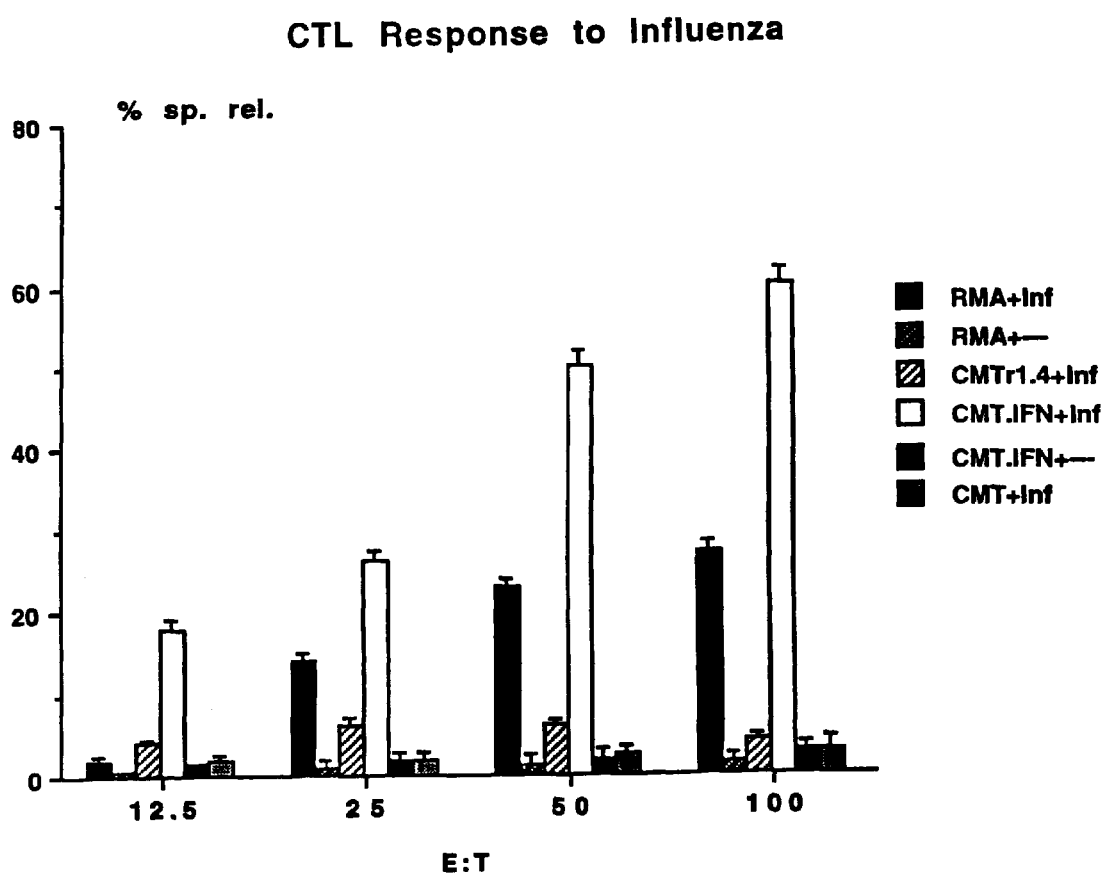
FIG. 17 is a histogram showing that RMA cells and CMT.64 cells treated with IFN-γ are recognized efficiently after influenza infection and CMT.64 cells transfected with the rat TAP-1 gene are not recognized

The results illustrated in FIG. 13 show that TAP-1 transfected CMT.64 cells (clones CMT-r1.1, r1-4 and r1-10) efficiently present antigen to VSV specific CTL. Introduction of TAP-1 into CMT.64 cells restores antigen presentation following VSV infection. Wild type CMT.64 cells and vector transfected CMT cells infected with VSV are not recognised by CTL. FIG. 17 shows that Influenza virus is not presented to specific CTL by CMT-TAP-1 cells. CMT. 64, RMA and CMTr1.4 cells were infected with Influenza virus and exposed to influenza-specific CTL. In this case however there was no recognition of the CMT-TAP-1 cells. Both positive controls, RXA and CMT.64+Inf, were efficiently lysed by the CTL.

Figure 14:
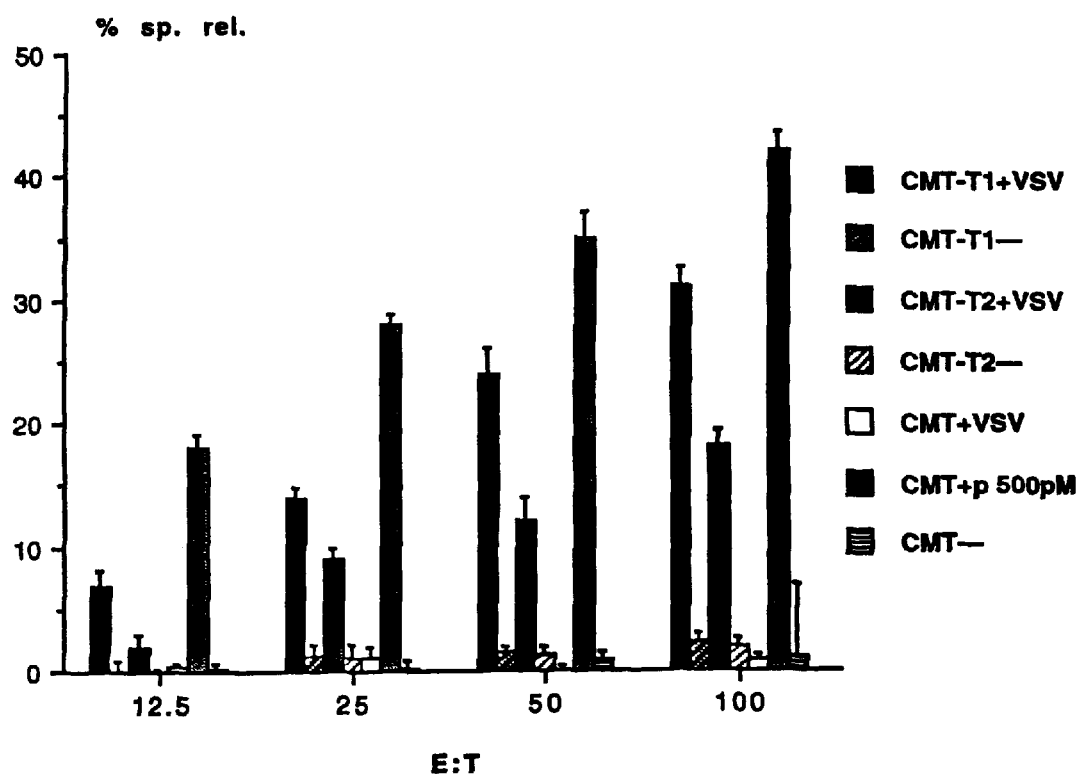
FIG. 14 is a histogram showing that TAP-1 transfected CMT.64 cells efficiently present antigen to VSV specific CTL.
Figure 15:
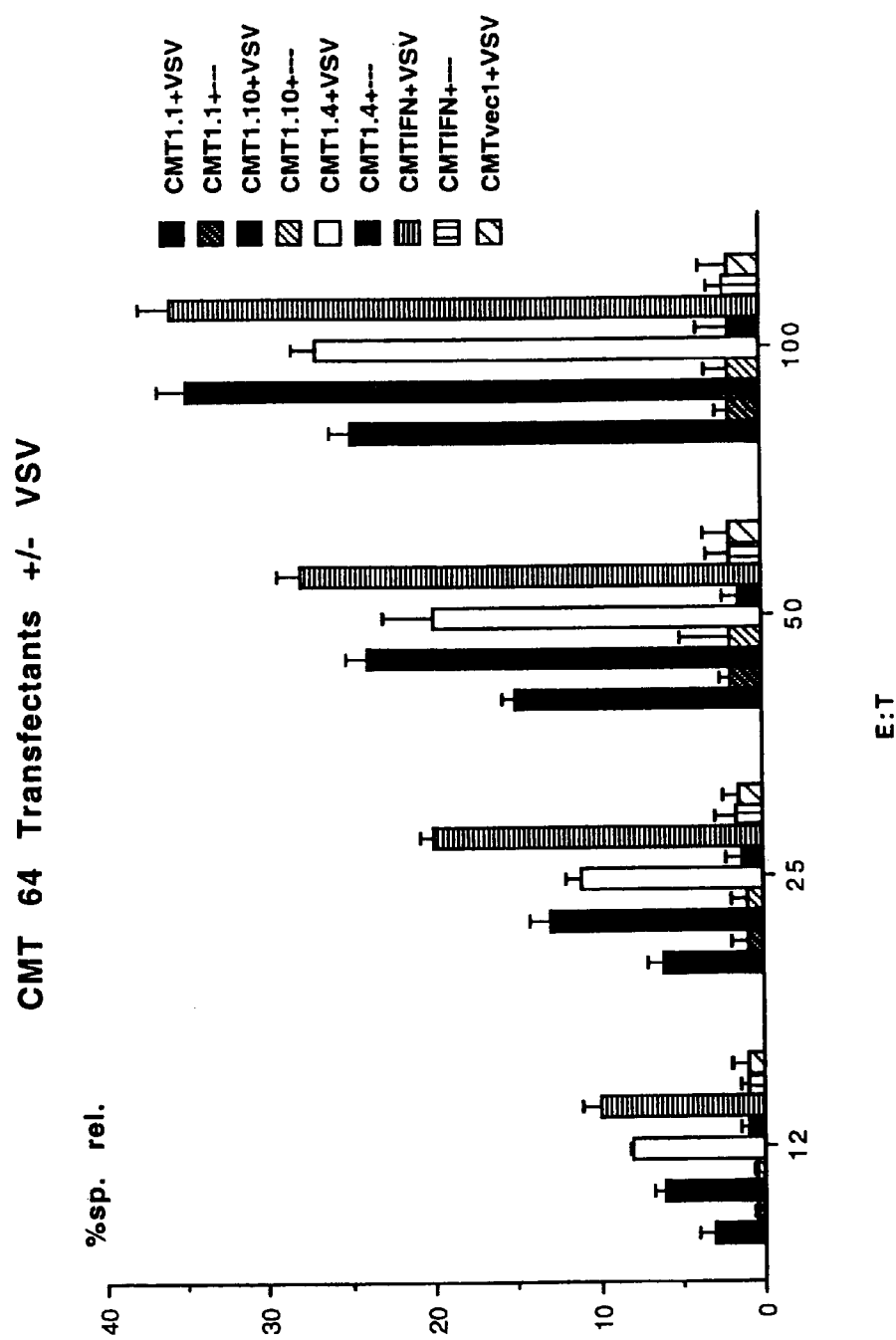
FIG. 15 is a histogram showing that TAP-1 transfected clones efficiently present antigen to VSV specific CTL.

Additional experiments were carried out showing that VSV expression requires only the expression of the TAP-1 transporter, and that recognition of CMT.64 cells expressing the rat TAP-1 gene alone is almost as efficient as cells expressing both transporters, TAP-1 and TAP-2. Expression of TAP-2 alone did not appear to be as efficient (FIG. 14). Different rat TAP-1 clones were also analyzed and confirmed the previous conclusions (FIG. 15).

Figure 16:
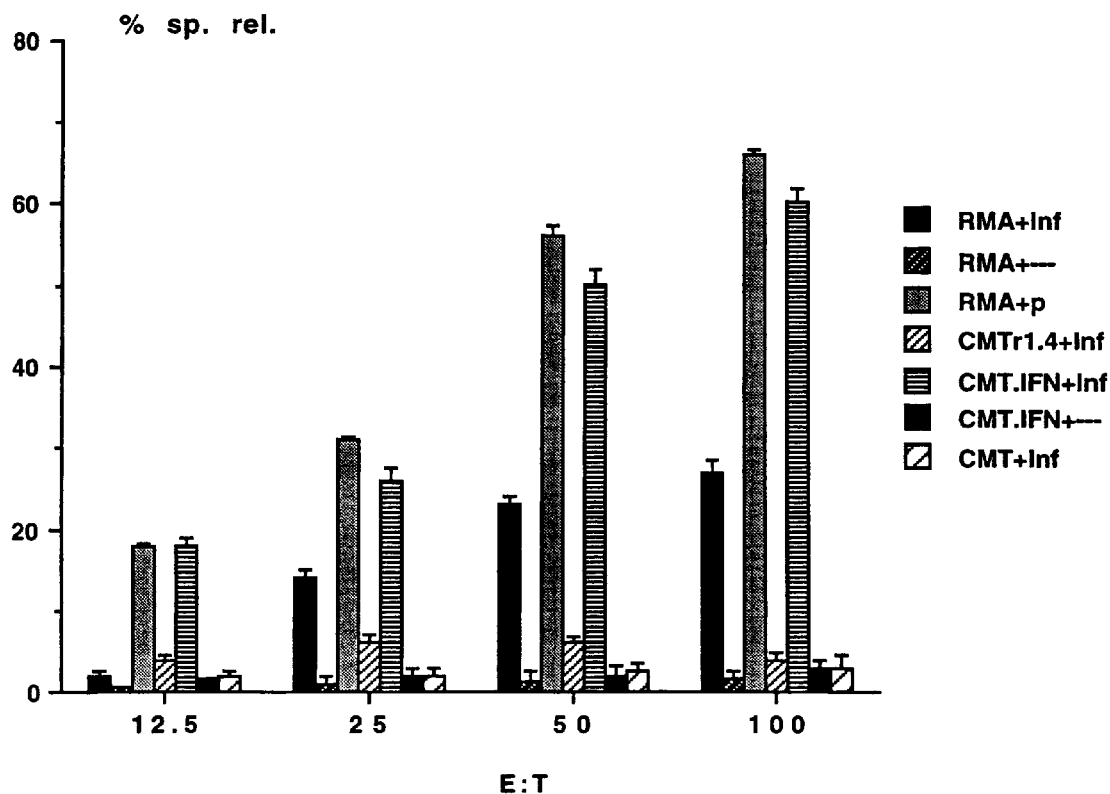
FIG. 16 is a histogram showing that RMA cells and CMT.64 cells treated with IFN-γ are recognized efficiently after influenza infection and CMT.64 cells transfected with the rat TAP-1 gene are not recognized.
Figure 18:
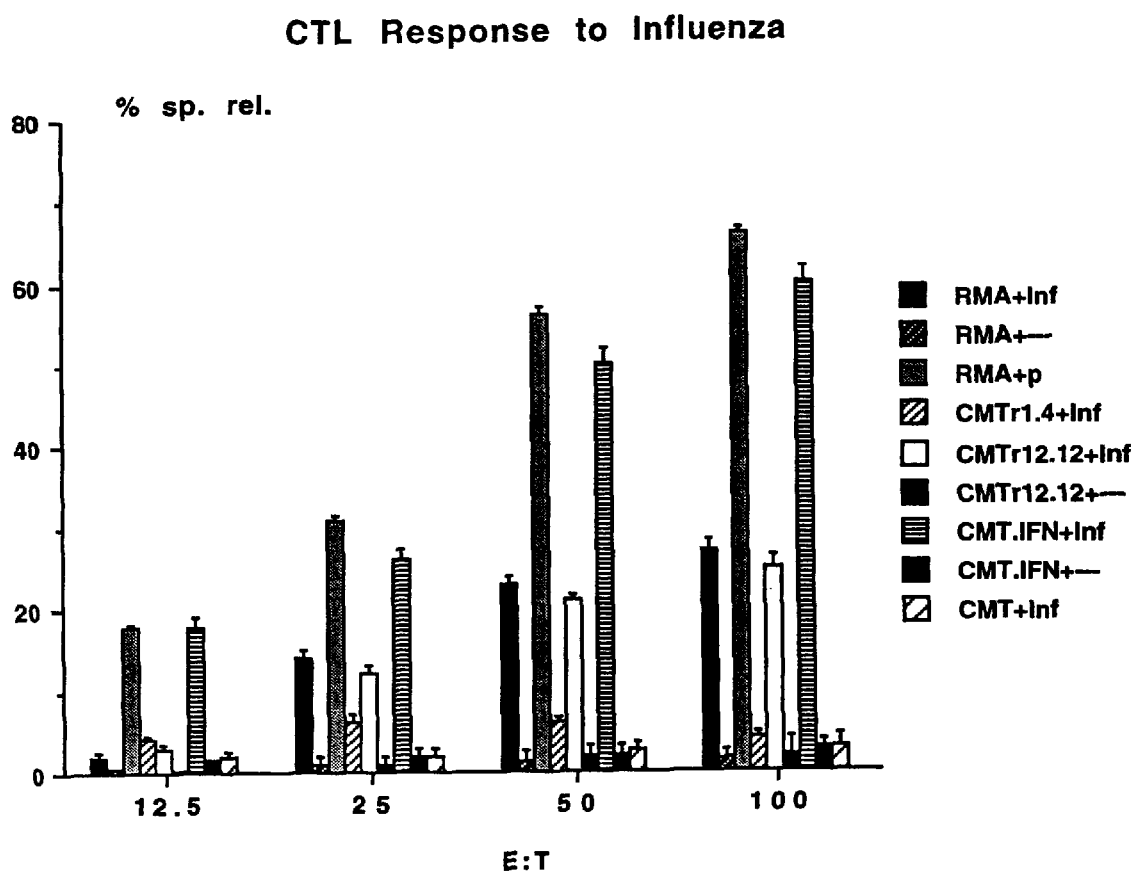
FIG. 18 is a histogram showing that RMA cells and CMT.64 cells treated with IFN-γ, CMT.64 cells transfected with both rat TAP genes are recognized after influenza virus infection.
Figure 19:
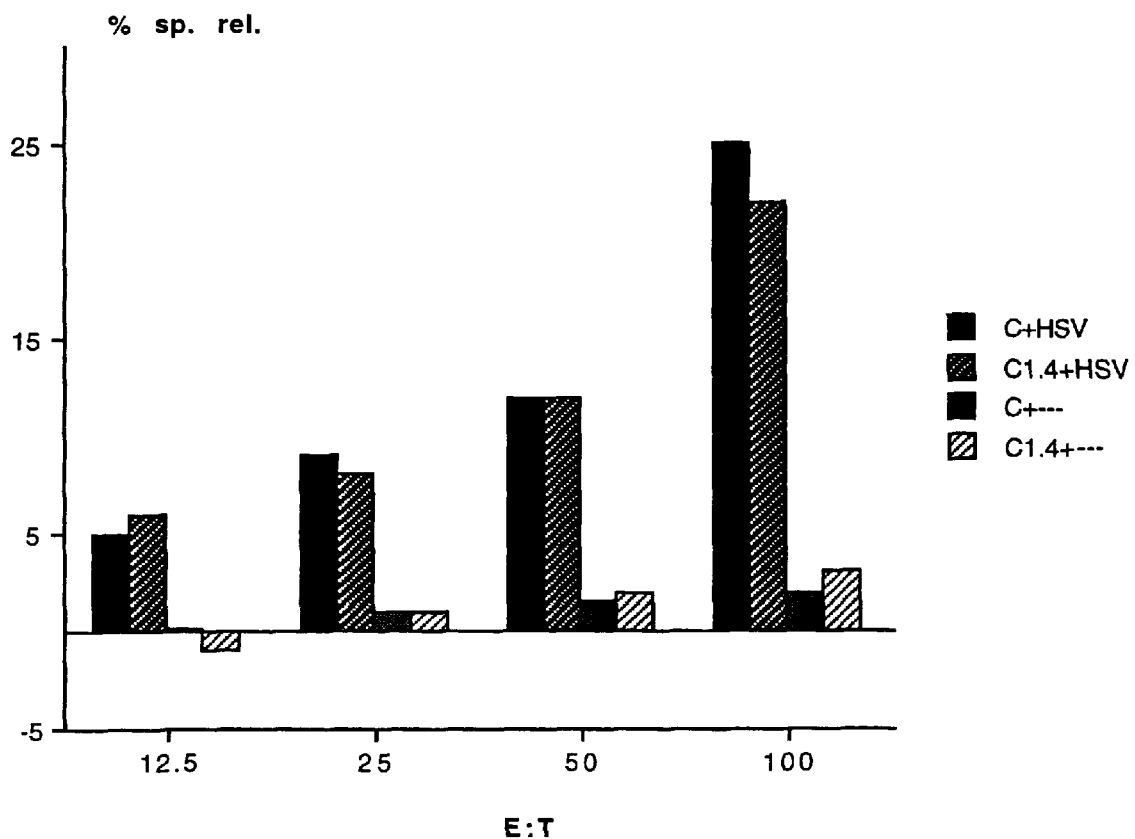
FIG. 19 is a histogram showing that HSV infected cells are recognized by specific CTL independently of the expression of the rat TAP-1 and/or TAP-2 transporter genes.

Influenza virus infected cells were found to be efficiently recognized only if both rat TAP genes are present (FIGS. 16 to 18). FIG. 16 shows that RMA cells and CMT.64 cells treated with IFN-γ are recognized efficiently after influenza infection. CMT.64 cells transfected with the rat TAP-1 gene are not recognized. FIG. 17 shows the same results observed in a second independent experiment. FIG. 18 shows that in addition to RMA cells and CMT.64 cells treated with IFN-γ, CMT.64 cells transfected with both rat TAP genes are recognized after influenza virus infection. FIG. 19 shows that HSV infected cells are recognized by specific CTL independently of the expression of the rat TAP-1 and/or TAP-2 transporter genes.

These results provide evidence that an individual TAP-1 transporter molecule can restore the antigen presentation capability to a deficient cell in the absence of TAP-2. This finding correlates with the recent observation that the TAP-1 protein interacts with MHC class I heavy chain in cells that do not express TAP-2 (Suh, W-K., et al. *Science* 264:1322–1326, 1994). This calls into question the absolute requirement for heterodimer formation between the two putative transporter molecules and demonstrates that different forms of transporter complex are functional and mediate transport of distinct subsets of the antigenic peptide pool for assembly with MHC class I molecules.

Example 13
Effects of TAP on Tumor Survival

Mice were injected with CMT.64 cells or CMT.12.12 cells (a rat TAP-1 and TAP-2 transfected clone) ip at $2 \times 10^5$ and $5 \times 10^5$ cells per mouse. The cell lines were resuspended in PBS prior to inoculation into recipient mice. The results are shown in Table 2. One of the mice treated with $5 \times 10^5$ CMT.64 cells was sacrificed and an autopsy clearly revealed the presence of a solid tumor at the site of injection. Furthermore, all mesenteric lymph nodes were grossly enlarged.

Example 14

The following is an experimental approach for finding peptides translocated in the ER by TAP-1 transporters, TAP-2 transporters and TAP-1-TAP-2 transporters.
1. Use of cell lines expressing TAP-1, TAP-2 and TAP-1 TAP-2 transporters; for example CMT.64 cells transfected with CDNA from TAP-1 and TAP-2, CMT.64, CMT.1-4, CMT.2-10, CMT.12-12.
2. Subcellular fractionation of these cells.
3. Isolation of the ER (endoplasmic reticulum).
4. Extraction of the peptides from the ER in 0.1% TFA.
5. Gel filtration.
6. Reverse-Phase HPLC.
7. Fractions can be collected and tested for CTL sensitization or for radioactivity if cells were labelled.
8. Finally, sequenced for amino acid.

Comparison of HPLC profile from different cell lines expressing different TAP transporters will provide information about peptide transport dependency on TAP molecules. Peaks of peptide can be isolated and analyzed. Sequencing of the peptides will provide information on the motif necessary for transport using TAP-1 alone, TAP-2 alone or TAP-1 and TAP-2 molecules. The protocol for peptides analysis and sequencing is standard and described in Rammensee papers and in Engelhard's papers.

Example 16
Anti-Sense Knockout in RMA-S Cells

This preliminary experiment was carried out on bulk selected populations of cells. The construct used was the same pHβA-neo that all the MTP 1 and 2 clones were obtained with as described above. In this study the MTP1 cDNA insert was cut out and it was replaced with a sequence in the opposite orientation. RMA-S cells only have TAP-1 not TAP-2, so only the MTP1 antisense was used. The data below are from single-colour FACS analysis, the numbers are linear (5000 events counted/sample). The 28.14.8s antibody is specific for $D^b$, and the Y-3 antibody is specific for $K^b$. The antisense construct is designated RMA-S.ptml.

| CELL | ANTIBODY | MEAN FLUORESCENCE |
|---|---|---|
| RMA-S | — | 56.6 |
| RMA-S | 28.14.8s | 129.9 |
| RMA-S | Y-3 | 222.2 |
| RMA-S.ptml | — | 53.4 |
| RMA-S.ptml | 28.14.85 | 96.7 |
| RMA-S.ptml | Y-3 | 148.9 |

Example 17
Effect of TAP-1 and TAP-2 on Survival of Mice Injected With Tumor Cells The survival of syngeneic C57BL/6 and control allogeneic Balb/C mice injected with very high doses of CMT.64 cells (from C57BL/6 mice) or CMT.12.12 cells (CMT.64 cells transfected with TAP-1 and TAP-2) was investigated as follows.

$5 \times 10^5$ CMT.64 or CMT.12.12 cells were injected into the mice intraperitoneally and the mice were followed for 90 days. Mice were autopsied after death or after 90 days. Survival of the mice is shown in FIG. 20. Results of the autopsies are summarized in Table 3. All of the syngeneic C57BL/6 mice injected with CMT.64 cells were dead before 60 days. These mice were found to have invasive generalised metastasized tumors throughout the body, and exhibited ruptured organs and/or perforated intestines with excessive fluid in the peritoneal cavity. This was classed as type B pathology. Approximately 20% of the syngeneic mice injected with CMT.12.12 cells were alive at 60 days and 3 out of 20 were alive at 90 days. Seventeen of these mice out of a total 20 had type B pathology two had no apparent pathology and one had type A pathology, described below.

Approximately 70% of the allogeneic control mice injected with CMT.64 cells were alive at 90 days exhibiting no significant pathology. The few mice which did exhibit any pathology had only small tumors (4–15 mm) at the site of the injection. This was classed as type A pathology. 100% of the allogeneic mice injected with CMT.12.12 cells were alive at 90 days, exhibiting no pathology.

The results show that syngeneic mice injected with CMT.12.12 cells survived longer than those transfected with CMT.64 cells, probably due to improved MHC Class I antigen presentation and recognition by the host immune system. The syngeneic mice transfected with CMT.12.12 surviving at 90 days showed no or little pathology.

TABLE 1

Peptides (p), hβ$_2$m (β$_2$m), and IFN-γ (IFN) Treatment Modifies the Conformation of $K^b$ and $D^b$ expressed on the cell surface of RMA, RMA-S, and CMT.64 Cells.

| | | | | Antibodies | | |
|---|---|---|---|---|---|---|
| | Treatment | | | 142-23.3 $K^b$ spec. | 28-11-5s $D^b$ spec. | BBM.1 hβ$_2$m spec. |
| Cell lines | IFN | p | β$_2$m | Arbitrary fluorescence units | | |
| Experiment 1 | | | | | | |
| CMF64 | − | − | − | 5 | 3 | ND |
| | − | + | + | 8 | 5 | ND |
| | + | − | − | 26 | 58 | ND |
| | + | + | + | 35 | 53 | ND |

TABLE 1-continued

Peptides (p), hβ₂m (β₂m), and IFN-γ (IFN) Treatment Modifies the Conformation of K$^b$ and D$^b$ expressed on the cell surface of RMA, RMA-S, and CMT.64 Cells.

| | Treatment | | | Antibodies | | |
|---|---|---|---|---|---|---|
| | | | | 142-23.3 K$^b$ spec. | 28-11-5s D$^b$ spec. | BBM.1 hβ₂m spec. |
| Cell lines | IFN | p | β₂m | Arbitrary fluorescence units | | |
| Experiment 2 | | | | | | |
| RMA | + | − | − | 346 | 430 | 6 |
| | + | + | − | 606 | 449 | 4 |
| | + | − | + | 438 | 549 | 406 |
| | + | + | + | 780 | 515 | 606 |
| RMA-S | + | − | − | 12 | 4 | 14 |
| | + | + | − | 10 | 1 | 14 |
| | + | − | + | 10 | 2 | 76 |
| | + | + | + | 41 | 2 | 262 |
| Experiment 3 | | | | | | |
| RMA | − | − | − | 164 | 173 | 1 |
| | − | + | + | 242 | 182 | 274 |
| RMA-S | − | − | − | 12 | 2 | 1 |
| | − | + | + | 70 | 2 | 86 |

TABLE 2

Effect of TAP 1 and TAP 2 on Tumor Survival

Mice were injected with CMT.64, or CMT.12.12 cells ip at $2 \times 10^5$ and $5 \times 10^5$ cells per mouse. The cell lines were resuspended in PBS prior to inoculation into recipient mice.

Preliminary Results

| | CMT.64 surv./total | CMT12.12 surv./total |
|---|---|---|
| 2 × 10⁵ | 0/5 | 2/5 |
| 5 × 10⁵ | 1/4* | 5/5 |

*One of the mice was sacrificed and an autopsy clearly revealed the presence of a solid tumor at the site of injection. Furthermore, all mesenteric lymph nodes were grossly enlarged

TABLE 3

AUTOPSY TUMOR RESULTS FROM CMT.64, CMT.12.12 EXPT. #1

| | C57BL/6 CMT.64 | CMT.12.12 | PBS | Balb/C CMT.64 | CMT. 12.12 |
|---|---|---|---|---|---|
| #Mice/exp. | 20 | 20 | 5 | 19 | 20 |
| Survived 90 Days | | 2-none 1-type A | 5-none | 13-none 1-type A | 20-none |
| Died Before 90 Days | 20-type B | 17-type B | | 4-type A 1-? | |

---

We claim:

1. A method of augmenting an immune response of a mammal to a tumor cell expressing low or nondetectable levels of MHC Class I molecules bearing T cell receptor interactive antigens comprising: introducing ex-vivo a nucleic acid molecule comprising a sequence encoding TAP-1 into the tumor cell under control of a suitable promoter; expressing TAP-1 in the tumor cell under suitable conditions, thereby enhancing processing and presentation of MHC Class I molecules bearing T cell receptor interactive antigens permitting recognition of the tumor by the mammal's immune response, wherein the immune response is augmented, and introducing the tumor cell into the mammal.

2. A method according to claim 1 wherein the tumor cell has low or non-detectable levels of TAP-1 and TAP-2 prior to introduction of the nucleic acid molecule.

3. A method according to claim 1 wherein the nucleic acid molecule further comprises a nucleic acid molecule encoding an antigenic peptide.

4. A method according to claim 1 wherein the nucleic acid molecule introduced into the tumor cell is a viral vector.

5. A method according to claim 4 wherein the vector is a vaccinia virus.

6. A method according to claim 1 wherein the immune response is a cytolytic T lymphocyte response.

7. A method of augmenting an immune response of a mammal to a tumor cell expressing low or nondetectable levels of MHC Class I molecules bearing T cell receptor interactive antigens comprising: introducing a vaccinia virus comprising a nucleic acid molecule comprising a sequence encoding TAP-1 into the tumor cell under control of a suitable promoter and; expressing TAP-1 in the tumor cell under suitable conditions, thereby enhancing processing and presentation of MHC Class I molecules bearing T cell receptor interactive antigens permitting recognition of the tumor by the mammal's immune response, wherein the immune response is augmented.

8. A method according to claim 7 wherein the tumor cell has low or non-detectable levels of TAP-1 and TAP-2 prior to introduction of the vaccinia virus.

9. A method according to claim 7 wherein the nucleic acid molecule further comprises a nucleic acid molecule encoding an antigenic peptide.

10. A method according to claim 7 wherein the immune response is a cytolytic T lymphocyte response.

* * * * *

SEQUENCE LISTING

<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: TAP-1

<400> SEQUENCE: 1

Arg Gly Tyr Val Tyr Gln Gly Leu
1               5

<210> SEQ ID NO 2
<211> LENGTH: 9
<212> TYPE: PRT
<213> ORGANISM: Artificial Sequence
<220> FEATURE:
<223> OTHER INFORMATION: TAP-2

<400> SEQUENCE: 2

Ala Ser Asn Glu Asn Met Glu Thr Met
1               5